United States Patent
Watanabe

(10) Patent No.: US 12,281,345 B2
(45) Date of Patent: *Apr. 22, 2025

(54) METHOD FOR PRODUCING 3,5-DIHYDROXY-4-METHOXYBENZYL ALCOHOL FROM PLANKTON

(71) Applicant: WATANABE OYSTER LABORATORY, CO., LTD., Tokyo (JP)

(72) Inventor: Mitsugu Watanabe, Tokyo (JP)

(73) Assignee: WATANABE OYSTER LABORATORY CO., LTD., Tokyo (JP)

( * ) Notice: Subject to any disclaimer, the term of this patent is extended or adjusted under 35 U.S.C. 154(b) by 539 days.

This patent is subject to a terminal disclaimer.

(21) Appl. No.: 17/778,201

(22) PCT Filed: Dec. 4, 2019

(86) PCT No.: PCT/JP2019/047379
§ 371 (c)(1),
(2) Date: May 19, 2022

(87) PCT Pub. No.: WO2021/100210
PCT Pub. Date: May 27, 2021

(65) Prior Publication Data
US 2022/0389463 A1    Dec. 8, 2022

(30) Foreign Application Priority Data
Nov. 20, 2019 (JP) .................... 2019-209288

(51) Int. Cl.
*C12N 1/12* (2006.01)
*C12P 7/18* (2006.01)
*C12P 7/22* (2006.01)

(52) U.S. Cl.
CPC . *C12P 7/18* (2013.01); *C12N 1/12* (2013.01)

(58) Field of Classification Search
CPC ..... C12P 7/18; C12P 7/22; C12N 1/12; C12N 1/066; C12N 1/10; C12R 2001/89; C12R 2001/90; C07C 41/01; C07C 43/23; C07C 41/34
See application file for complete search history.

(56) References Cited

U.S. PATENT DOCUMENTS

2016/0200653 A1    7/2016 Watanabe et al.

FOREIGN PATENT DOCUMENTS

| EP | 2 669 353 | 12/2013 |
| JP | 2016-42825 | 4/2016 |
| JP | 6632010 | 1/2020 |
| WO | 2016/009594 | 1/2016 |

OTHER PUBLICATIONS

Mitsugu Watanabe et al., "A phenolic antioxidant from the Pacific oyster (*Crassostrea gigas*) inhibits oxidation of cultured human hepatocytes mediated by diphenyl-1-pyrenylphosphine", Food Chemistry, vol. 134, (2012), pp. 2086-2089.

Mitsugu Watanabe et al., "Isolation and Characterization of a Phenolic Antioxidant from the Pacific Oyster (*Crassostrea gigas*)", J. Agric. Food Chem., (2012), vol. 60, pp. 830-835.

International Search Report (ISR) issued Feb. 18, 2020 in International (PCT) Application No. PCT/JP2019/047379.

Hiroaki Okabe et al., "Mass Spectrometric Quantification of Amphipathic, Polyphenolic Antioxidant of the Pacific Oyster (*Crassostrea gigas*)", Analytical Sciences, vol. 31, pp. 1341-1344, Dec. 2015, cited in ISR.

*Primary Examiner* — Satyendra K Singh
(74) *Attorney, Agent, or Firm* — Wenderoth, Lind & Ponack, L.L.P.

(57) ABSTRACT

[Problem] It is an object of the present invention to provide a method for collecting seawater that contains plankton and producing DHMBA, which is an antioxidant, from the plankton contained in the seawater.

[Solution] The method of the present invention includes: filtering collected seawater containing the plankton using a filter; taking out a cell content from the plankton remaining on the filter; subsequently heating/pressurizing the cell content taken out; and producing 3,5-dihydroxy-4-methoxybenzyl alcohol from the heated/pressurized product. The plankton is a diatom.

13 Claims, 27 Drawing Sheets

Fig.4

RESULT OF HEATING EXPERIMENT

| TEMPERATURE | ATMOSPHERIC PRESSURE | PERIOD | EXTRACTION PERIOD | | | | | |
|---|---|---|---|---|---|---|---|---|
| | | | 30 MINUTES | ONE HOUR | TWO HOURS | THREE HOURS | FOUR HOURS | FIVE HOURS |
| 60 | 1 | DETECTED OR NOT | × | ○ | ○ | ○ | ○ | × |
| | | CONCENTRATION (mg/L) | - | 0.0053 | 0.0064 | 0.0059 | 0.0063 | - |
| 80 | 1 | DETECTED OR NOT | ○ | ○ | × | ○ | ○ | ○ |
| | | CONCENTRATION (mg/L) | 0.0035 | 0.0053 | - | 0.0035 | 0.0045 | 0.0036 |

Fig.5

RESULT OF PRESSURIZING EXPERIMENT

| ATMOSPHERE PRESSURE | PERIOD | EXTRACTION PERIOD | | | | |
|---|---|---|---|---|---|---|
| | | 30 MINUTES | ONE HOUR | THREE HOURS | FIVE HOURS |
| 2 | DETECTED OR NOT | ◯ | | | |
| | CONCENTRATION (mg/L) | 0.0125 | | | |
| 2.5 | DETECTED OR NOT | ◯ | ◯ | ◯ | ◯ |
| | CONCENTRATION (mg/L) | 0.197 | 0.355 | 0.483 | 0.683 |
| 3 | DETECTED OR NOT | ◯ | ◯ | ◯ | ◯ |
| | CONCENTRATION (mg/L) | 0.282 | 0.938 | 1.925 | 1.341 |

Fig. 8

H7-09-18S
Search condition: Limit to sequences from type material

| Sequence number | Number by Max score | Description | Max score | Total score | Query cover | E value | Ident | Accession | |
|---|---|---|---|---|---|---|---|---|---|
| 1 | 1 | Fistulifera solaris gene for 18S ribosomal RNA, partial sequence | 1027 | 1027 | 100.00% | 0 | 93.88% | AB769357.1 | Bacillariophyta |
| 2 | 2 | Pedospumella encystans voucher B 40 G040871 18S ribosomal RNA gene, partial sequence | 843 | 843 | 100.00% | 0 | 89.06% | AY651083.1 | Golden algae |
| 3 | 3 | Heterococcus fuornensis partial 18S rRNA gene, strain SAG 835-5 | 832 | 832 | 100.00% | 0 | 88.71% | AM490821.1 | Yellow-green algae |
| 4 | 3 | Heterococcus caespitosus partial 18S rRNA gene, strain SAG 835-2a | 832 | 832 | 100.00% | 0 | 88.71% | AM490820.1 | Yellow-green algae |
| 5 | 5 | Chlorellidium tetrabotrys SAG811-1 18S ribosomal RNA gene, partial sequence | 821 | 821 | 100.00% | 0 | 88.45% | FJ030892.1 | Yellow-green algae |
| 6 | 5 | Spumella vulgaris isolate 199hm 18S ribosomal RNA gene, partial sequence | 821 | 821 | 100.00% | 0 | 88.47% | DQ388582.1 | Golden algae |
| 7 | 7 | Spiaerosyrus composita partial 18S rRNA gene, strain SAG 53.91 | 809 | 809 | 100.00% | 0 | 88.12% | AJ579333.1 | |
| 8 | 8 | Bumilleriopsis pyrenoidosa partial 18S rRNA gene, strain SAG 69.90 | 802 | 802 | 100.00% | 0 | 87.09% | AJ579332.1 | |
| 9 | 9 | Pseudotetraedriella kamilae strain SAG 2056 18S ribosomal RNA gene, partial sequence | 778 | 778 | 100.00% | 0 | 87.39% | EF044311.1 | |
| 10 | 10 | Nannochloropsis limnetica strain SAG 18.99 culture-collection SAG:18.99 18S ribosomal RNA gene, partial sequence | 778 | 778 | 100.00% | 0 | 87.41% | AF251496.1 | |
| 11 | 11 | Monodus unipapila partial 18S rRNA gene, strain SAG 8.83 | 767 | 767 | 100.00% | 0 | 97.11% | AM490827.1 | |
| 12 | 12 | Vischeria helvetica strain SAG 876-1 18S ribosomal RNA gene, complete sequence | 763 | 763 | 100.00% | 0 | 86.98% | JX188080.1 | |
| 13 | 13 | Eustigmatos polyphem strain SAG 38.84 18S ribosomal RNA gene, partial sequence | 758 | 758 | 100.00% | 0 | 86.84% | AM490823.1 | |
| 14 | 14 | Eustigmatos polyphem strain SAG 38.84 18S ribosomal RNA gene, complete sequence | 750 | 750 | 100.00% | 0 | 86.84% | JX188077.1 | |
| 15 | 15 | Ochromonas danica strain SAG933 7 18S ribosomal RNA gene, partial sequence | 749 | 749 | 96.00% | 0 | 96.62% | JQ281514 | |
| 16 | 16 | Monodus unipapila culture SAG:8.83 voucher SAG:8.83 18S ribosomal RNA (ssu) gene, partial sequence | 728 | 728 | 100.00% | 0 | 86.89% | HQ710565.1 | |
| 17 | 17 | Sargassococcus simulans strain CCMP1996 18S ribosomal RNA gene, partial sequence | 719 | 719 | 100.00% | 0 | 85.88% | MF927481.1 | |
| 18 | 17 | Pelagospius aureus strain CCMP1410 18S ribosomal RNA gene, partial sequence | 719 | 719 | 100.00% | 0 | 85.90% | MF927480.1 | |
| 19 | 19 | Sargassococcus epiphyticus strain CCMP1895 18S ribosomal RNA gene, partial sequence | 708 | 708 | 100.00% | 0 | 85.53% | MF927478.1 | |
| 20 | 20 | Lagenidium sp. PWL-2010c strain GBS 127042 18S small subunit ribosomal RNA gene, partial sequence | 686 | 686 | 100.00% | 0 | 84.89% | HQ384409.1 | |
| 21 | 21 | Geranomyces variabilis voucher MP63 18S small subunit ribosomal RNA gene, partial sequence | 682 | 682 | 100.00% | 0 | 84.94% | HQ901737.1 | |
| 22 | 21 | Desmosporangium alabamae voucher JEL563 18S small subunit ribosomal RNA gene, partial sequence | 682 | 682 | 100.00% | 0 | 84.94% | HQ901742.1 | |
| 23 | 21 | Spumella rivalis strain AR4A6 18S ribosomal RNA gene, partial sequence | 682 | 682 | 99.00% | 0 | 85.65% | GU073468.1 | |
| 24 | 24 | Finnicolochytrium jonesii strain JEL 569 18S rRNA gene, partial sequence from TYPE material | 671 | 671 | 100.00% | 0 | 84.65% | NG_061114.1 | |
| 25 | 24 | Thoreauomyces humboldtii JEL 95 18S rRNA gene, partial sequence from TYPE material | 671 | 671 | 100.00% | 0 | 84.63% | NG_061113.1 | |
| 26 | 24 | Rhizoclosmatium jonesii voucher JEL569 18S small subunit ribosomal RNA gene, partial sequence | 671 | 671 | 100.00% | 0 | 84.65% | HQ901746.1 | |
| 27 | 24 | Thoreauomyces humboldtii voucher JEL95 18S small subunit ribosomal RNA gene, partial sequence from TYPE material | 671 | 671 | 100.00% | 0 | 84.63% | HQ901727.1 | |
| 28 | 28 | Finnicolochytrium alabamae voucher JEL 538 18S rRNA gene, partial sequence from TYPE material | 665 | 665 | 100.00% | 0 | 84.51% | NG_062391.1 | |
| 29 | 28 | Finnicolochytrium alabamae voucher JEL538 18S small subunit ribosomal RNA gene, partial sequence | 665 | 665 | 100.00% | 0 | 84.51% | HQ901734.1 | |
| 30 | 29 | Myxozyma neglecta 18S rRNA gene, partial sequence from TYPE material | 645 | 645 | 99.00% | 0 | 84.03% | NG_062046.1 | |
| 31 | 29 | Myxozyma mucilagina 18S rRNA gene, partial sequence from TYPE material | 645 | 645 | 99.00% | 0 | 84.03% | NG_062045.1 | |
| 32 | 29 | Myxozyma neglecta strain NRRL Y-27508 18S ribosomal RNA gene, partial sequence | 645 | 645 | 99.00% | 0 | 84.03% | DQ519022.1 | |
| 33 | 29 | Myxozyma mucilagina strain NRRL Y-11833 18S ribosomal RNA gene, partial sequence | 645 | 645 | 99.00% | 0 | 84.03% | DQ519021.1 | |

Fig.9

H7-09-28S_D2R2
Search condition: Limit to sequences from type material

| Sequence number | Number by Max score | Description | Max score | Total score | Query cover | E value | Ident | Accession | |
|---|---|---|---|---|---|---|---|---|---|
| 1 | 1 | Chlorellidium tetrabotrys strain SAG811-1 28S ribosomal RNA gene, partial sequence | 233 | 233 | 48.00% | 2.0E-58 | 84.94% | FJ830881.1 | Yellow-green algae |
| 2 | 2 | Fimicolochytrium jonesii JEL 569 28S rRNA gene, partial sequence; from TYPE material | 224 | 224 | 48.00% | 1.0E-55 | 84.26% | NG_060391.1 | Fungus |
| 3 | 2 | Fimicolochytrium jonesii voucher JEL569 28S large subunit ribosomal RNA gene, partial sequence | 224 | 224 | 48.00% | 1.0E-53 | 84.26% | HQ901681.1 | Fungus |
| 4 | 4 | Hyaloraphidium curvatum voucher MP03 28S large subunit ribosomal RNA gene, partial sequence | 219 | 219 | 48.00% | 5.0E-54 | 84.03% | HQ901692.1 | Fungus |
| 5 | 5 | Thoreauomyces humboldtii JEL 95 28S rRNA gene, partial sequence; from TYPE material | 217 | 217 | 48.00% | 2.0E-53 | 83.90% | NG_059935.1 | Fungus |
| 6 | 5 | Thoreauomyces humboldtii voucher JEL 95 28S large subunit ribosomal RNA gene, partial sequence | 217 | 217 | 48.00% | 2.0E-53 | 83.90% | HQ901662.1 | Fungus |
| 7 | 5 | Spizellomyces acuminatus 28S ribosomal RNA (LSU) gene, partial sequence | 217 | 217 | 48.00% | 2.0E-53 | 83.83% | JN941010.1 | |
| 8 | 5 | Phlyctochytrium africanum voucher CBS 454.65 28S ribosomal RNA gene, partial sequence | 217 | 217 | 48.00% | 2.0E-53 | 83.83% | FJ827693.1 | |
| 9 | 9 | Holtermanniella kwittica CBS 9496 28S rRNA gene, partial sequence; from TYPE material | 215 | 215 | 48.00% | 6.0E-53 | 83.61% | NG_058307.1 | |
| 10 | 9 | Holtermanniella wattica CBS 9496 large subunit ribosomal RNA gene, partial sequence | 215 | 215 | 48.00% | 6.0E-53 | 83.61% | KY107874.1 | |
| 11 | 11 | Fimicolochytrium alabamae JEL 528 28S rRNA gene, partial sequence; from TYPE material | 213 | 213 | 48.00% | 2.0E-52 | 83.46% | NG_060390.1 | |
| 12 | 11 | Fimicolochytrium alabamae voucher JEL538 28S large subunit ribosomal RNA gene, partial sequence | 213 | 213 | 48.00% | 2.0E-52 | 83.40% | HQ901669.1 | |
| 13 | 11 | Gorgonomyces haynaldii BAFC ARG 026 28S rRNA gene, partial sequence; from TYPE material | 213 | 213 | 48.00% | 2.0E-52 | 83.62% | NG_042448.1 | |
| 14 | 14 | Cerporiopsis semisupina CBS 10822 28S rRNA gene, partial sequence; from TYPE material | 211 | 211 | 48.00% | 8.0E-52 | 83.40% | NG_064354.1 | |
| 15 | 14 | Gorgonopsis sp. CL2-2014 voucher Oxi 16822 28S large subunit ribosomal RNA gene, partial sequence | 211 | 211 | 48.00% | 8.0E-52 | 83.40% | KF845949.1 | |
| 16 | 14 | Sonoraphlyctis ranzonii DAOM BR 060 28S rRNA, partial sequence; from TYPE material | 211 | 211 | 48.00% | 8.0E-52 | 83.47% | NG_042454.1 | |
| 17 | 17 | Basidioascus undulatus strain CBS 1.87763 large subunit ribosomal RNA gene, partial sequence | 209 | 209 | 48.00% | 3.0E-52 | 83.19% | MH877552.1 | |
| 18 | 17 | Piskurozyma taiwanensis CBS 9813 28S rRNA gene, partial sequence; from TYPE material | 209 | 209 | 48.00% | 3.0E-51 | 83.19% | NG_058375.1 | |
| 19 | 17 | Coffeazyma gastrica CBS 2288 28S rRNA gene, partial sequence; from TYPE material | 209 | 209 | 48.00% | 3.0E-51 | 83.19% | NG_058296.1 | |
| 20 | 17 | Coffeazyma acidotolerans CBS 10877 28S rRNA gene, partial sequence; from TYPE material | 209 | 209 | 48.00% | 3.0E-51 | 83.19% | NG_058295.1 | |
| 21 | 17 | Solicoccozyma aeria culture CBS 155 large subunit ribosomal RNA gene, partial sequence | 209 | 209 | 48.00% | 3.0E-51 | 83.19% | KY109666.1 | |
| 22 | 17 | Piskurozyma taiwanensis culture CBS.9813 large subunit ribosomal RNA gene, partial sequence | 209 | 209 | 48.00% | 3.0E-51 | 83.19% | KY108924.1 | |
| 23 | 17 | Naganishia globosa culture CBS.5106 large subunit ribosomal RNA gene, partial sequence | 209 | 209 | 48.00% | 3.0E-51 | 83.19% | KY108616.1 | |
| 24 | 17 | Naganishia friedmannii culture CBS.7160 large subunit ribosomal RNA gene, partial sequence | 209 | 209 | 48.00% | 3.0E-51 | 83.19% | KY108613.1 | |
| 25 | 17 | Coffeazyma gastrica culture CBS.2288 large subunit ribosomal RNA gene, partial sequence | 209 | 209 | 48.00% | 3.0E-51 | 83.19% | KY107764.1 | |
| 26 | 17 | Coffeazyma acidotolerans culture CBS.10872 large subunit ribosomal RNA gene, partial sequence | 209 | 209 | 48.00% | 3.0E-51 | 83.19% | KY107763.1 | |
| 27 | 17 | Filobasidium wieringae culture CBS.1937 large subunit ribosomal RNA gene, partial sequence | 209 | 209 | 48.00% | 3.0E-51 | 83.12% | KY107733.1 | |
| 28 | 17 | Filobasidium magnum culture CBS.140 large subunit ribosomal RNA gene, partial sequence | 209 | 209 | 48.00% | 3.0E-51 | 83.12% | KY107722.1 | |
| 29 | 17 | Filobasidium globisporum culture CBS.7642 large subunit ribosomal RNA gene, partial sequence | 209 | 209 | 48.00% | 3.0E-51 | 83.12% | KY107713.1 | |
| 30 | 17 | Filobasidium floriforme culture CBS.6241 large subunit ribosomal RNA gene, partial sequence | 209 | 209 | 48.00% | 3.0E-51 | 83% | KY107703.1 | |

HI-05-18S
Search condition: Limit to sequences from type material

| Sequence number by Max score | Description | Max score | Total score | Query cover | E value | Ident. | Accession | |
|---|---|---|---|---|---|---|---|---|
| 1 | Fibuliflora solaris gene for 18S ribosomal RNA, partial sequence | 1521 | 1521 | 100.00% | 0 | 95.50% | AB183957.1 | Bacillariophyto |
| 2 | Pedospumella encystans voucher B.40.Ob40871 18S ribosomal RNA gene, partial sequence | 1511 | 1511 | 100.00% | 0 | 89.06% | KY651089.1 | Golden algae |
| 3 | Chlorellidium tetrabotrys strain SAG81-1 18S ribosomal RNA gene, partial sequence | 1506 | 1506 | 100.00% | 0 | 89.00% | FJ039872.1 | Yellow-green algae |
| 4 | Heterococcus hormoseiros partial 18S rRNA gene, strain SAG 835-5 | 1495 | 1495 | 100.00% | 0 | 89.00% | AM490802.1 | Yellow-green algae |
| 5 | Heterococcus caespitosus partial 18S rRNA gene, strain SAG 835-2a | 1486 | 1486 | 100.00% | 0 | 89.00% | AM490820.1 | Yellow-green algae |
| 6 | Sphaerosorus carogenita partial 18S rRNA gene, strain SAG 63.91 | 1486 | 1486 | 100.00% | 0 | 89.00% | AJ579333.1 | |
| 7 | Bumilleriopsis pyrenoidosa partial 18S rRNA gene, strain SAG 63.99 | 1478 | 1478 | 100.00% | 0 | 89.00% | AJ579332.1 | |
| 8 | Pseudobumilleriella lobata voucher wild isolate 18S ribosomal RNA gene, partial sequence | 1471 | 1471 | 100.00% | 0 | 89.00% | AF451496.1 | |
| 9 | Pseudostaurastrum Iimnetica strain SAG 2058 18S ribosomal RNA gene, partial sequence | 1454 | 1454 | 100.00% | 0 | 88.00% | EF044711.1 | |
| 10 | Vischeria helvetica strain SAG 130-1 18S ribosomal RNA gene, complete sequence | 1450 | 1450 | 100.00% | 0 | 89.00% | KX180080.1 | |
| 11 | Heterococcus viridis isolate SAG 860-1 18S ribosomal RNA gene, complete sequence | 1448 | 1448 | 100.00% | 0 | 88.00% | KX74398.1 | |
| 12 | Eustigmatos polyphem strain SAG 38.84 18S ribosomal RNA gene, complete sequence | 1445 | 1445 | 100.00% | 0 | 88.00% | KX180177.1 | |
| 13 | Squamalia vulgaris isolate 1995m 18S ribosomal RNA gene, partial sequence | 1443 | 1443 | 100.00% | 0 | 88.00% | DQ383352.1 | |
| 14 | Mendeka cespedia partial 18S rRNA gene, strain SAG 8.83 | 1431 | 1431 | 100.00% | 0 | 88.00% | AM490807.1 | |
| 15 | Dichtomomas danica strain SAG 833.7 18S rRNA gene, partial sequence | 1402 | 1402 | 100.00% | 0 | 88.00% | HG811114.1 | |
| 16 | Bumilleriopsis petersentiana partial 18S rRNA gene, strain SAG 809-3 | 1381 | 1381 | 100.00% | 0 | 87.00% | AJ579331.1 | |
| 17 | Pythium oopapillum 18S ribosomal RNA, partial sequence | 1335 | 1335 | 100.00% | 0 | 86.00% | LP780591.1 | |
| 18 | Sanguisorbus simulans strain CCMP1999 18S ribosomal RNA gene, partial sequence | 1317 | 1317 | 100.00% | 0 | 86.00% | MF974311.1 | |
| 19 | Poisprades aureus strain CCMP1418 18S ribosomal RNA gene, partial sequence | 1317 | 1317 | 100.00% | 0 | 86.00% | MF927499.1 | |
| 20 | Vidyana beta-vulgaris strain K814-M-PM-A 18S ribosomal RNA gene, partial sequence | 1312 | 1312 | 100.00% | 0 | 86.00% | MF910773.1 | |
| 21 | Sanguisorbus snadensis strain CCMP1935 18S ribosomal RNA gene, partial sequence | 1306 | 1306 | 100.00% | 0 | 86.00% | MF927478.1 | |
| 22 | Pythium grandisporangium strain CBS 286.79 18S ribosomal RNA gene, partial sequence; internal transcribed spacer 1, 5.8S ribosomal RNA gene, and internal transcribed spacer 2, complete sequence; and 28S ribosomal RNA gene, partial sequence | 1283 | 1283 | 100.00% | 0 | 86.00% | AY598692.2 | |
| 23 | Lagenidium giganteum f. caninum isolate C11-AK262 small subunit ribosomal RNA gene, partial sequence; internal transcribed spacer 1, 5.8S ribosomal RNA gene, and internal transcribed spacer 2, complete sequence; and large subunit ribosomal RNA gene, partial sequence | 1268 | 1268 | 100.00% | 0 | 88.10% | KF913305.2 | |
| 24 | Pythium parvum strain CBS 225.88 18S ribosomal RNA gene, partial sequence; internal transcribed spacer 1, 5.8S ribosomal RNA gene, and internal transcribed spacer 2, complete sequence; and 28S ribosomal RNA gene, partial sequence | 1288 | 1288 | 100.00% | 0 | 86.00% | AY598697.2 | |
| 25 | Pythium apleroticum strain CBS 215.80 18S ribosomal RNA gene, partial sequence; internal transcribed spacer 1, 5.8S ribosomal RNA gene, and internal transcribed spacer 2, complete sequence; and 28S ribosomal RNA gene, partial sequence | 1288 | 1288 | 100.00% | 0 | 86.00% | AY598632.2 | |
| 26 | Pythium plurisporium strain CBS 160530 18S ribosomal RNA gene, partial sequence; internal transcribed spacer 1, 5.8S ribosomal RNA gene, and internal transcribed spacer 2, complete sequence; and 28S ribosomal RNA gene, partial sequence | 1286 | 1286 | 100.00% | 0 | 86.00% | AY598684.2 | |
| 27 | Pythium debaryanum strain CBS 314.33 18S ribosomal RNA gene, partial sequence; internal transcribed spacer 1, 5.8S ribosomal RNA gene, and internal transcribed spacer 2, complete sequence; and 28S ribosomal RNA gene, partial sequence | 1284 | 1284 | 100.00% | 0 | 86.00% | AY598674.2 | |
| 28 | Pythium pythinum strain CBS 108.64 18S ribosomal RNA gene, partial sequence; internal transcribed spacer 1, 5.8S ribosomal RNA gene, and internal transcribed spacer 2, complete sequence; and 28S ribosomal RNA gene, partial sequence | 1279 | 1279 | 100.00% | 0 | 86.00% | AY598638.2 | |
| 29 | Pythium sphanodermatum strain CBS 110.80 18S ribosomal RNA gene, partial sequence; internal transcribed spacer 1, 5.8S ribosomal RNA gene, and internal transcribed spacer 2, complete sequence; and 28S ribosomal RNA gene, partial sequence | 1279 | 1279 | 100.00% | 0 | 86.00% | AY598622.2 | |
| 30 | Pythium rostrafingens voucher CBS 118454 18S ribosomal RNA gene, partial sequence, internal transcribed spacer 1, 5.8S ribosomal RNA gene, and internal transcribed spacer 2, complete sequence; and 28S ribosomal RNA gene, partial sequence | 1262 | 1262 | 100.00% | 0 | 86.10% | HQ643781.2 | |

Fig.14

H9-05-28S_D2C2
Search condition: Limit to sequences from type material

| Sequence number | Number by Max score | Description | Max score | Total score | Query cover | E value | Ident | Accession | |
|---|---|---|---|---|---|---|---|---|---|
| 1 | 1 | Nannochloropsis gaditana strain SAG2.99 28S ribosomal RNA gene, partial sequence | 193 | 193 | 36.00% | 3.00E-46 | 86.00% | FJ030380.1 | Nannochloropsis |
| 2 | 2 | Paraglomus occultum INVAM IA702 28S rRNA gene, partial sequence, from reference material | 187 | 187 | 64.00% | 1.00E-44 | 78.00% | NG_027367.1 | Fungus |
| 3 | 3 | Developayella elegans strain CCAP1917/1 28S ribosomal RNA gene, partial sequence | 183 | 183 | 79.00% | 2.00E-43 | 76.00% | FJ030882.1 | Oomycete |
| 4 | 4 | Saccharomyces dimmenae gene for LSU rRNA, partial sequence, strain: JCM 8762 | 169 | 169 | 23.00% | 5.00E-39 | 93.00% | AB644404.1 | Fungus |
| 5 | 4 | Saccharomyces cerevisiae genes for 18S rRNA, ITS1, 5.8S rRNA, ITS2, 28S rRNA, partial sequence and complete sequence | 169 | 169 | 23.00% | 5.00E-39 | 93.00% | AB638335.1 | Fungus |
| 6 | 6 | Pseudobensingtonia yapapatiae SFSU DED 8605 28S rRNA gene, partial sequence, from TYPE material | 167 | 167 | 33.00% | 2.00E-38 | 86.00% | NG_060106.1 | |
| 7 | 6 | Pseudobensingtonia yapapatiae voucher DED 8605 28S large subunit ribosomal RNA gene, partial sequence | 167 | 167 | 33.00% | 2.00E-38 | 86.00% | KC484300.1 | |
| 8 | 8 | Africastellanos koryama OSC 150014 28S ribosomal RNA gene, partial sequence, from TYPE material | 161 | 161 | 33.00% | 8.00E-37 | 85.00% | KX685720.1 | |
| 9 | 8 | Africastellanos koryama voucher OSC 150014 28S rRNA gene, partial sequence from TYPE material | 161 | 161 | 33.00% | 8.00E-37 | 85.00% | KX685595.1 | |
| 10 | 8 | Borofutus dhakanus HKAS 73785 28S rRNA 28S rRNA gene, partial sequence: from TYPE material | 161 | 161 | 33.00% | 8.00E-37 | 85.00% | NG_042663.1 | |
| 11 | 8 | Spongiforma squarepantsii voucher LHF814 28S rRNA gene, partial sequence | 161 | 161 | 33.00% | 8.00E-37 | 85.00% | HQ724509.1 | |
| 12 | 8 | Spongiforma thailandica BBH DED 7873 28S rRNA, partial sequence, from TYPE material | 161 | 161 | 33.00% | 8.00E-37 | 85.00% | NG_042484.1 | |
| 13 | 13 | Minimedusa polyspora strain CBS 113.16 large subunit ribosomal RNA gene, partial sequence | 158 | 158 | 33.00% | 1.00E-35 | 84.00% | MH866167.1 | |
| 14 | 13 | Malassezia equina CBS 9969 28S rRNA gene, partial sequence, from TYPE material | 158 | 158 | 34.00% | 1.00E-35 | 84.00% | NG_060248.1 | |
| 15 | 13 | Phyllozyma linderae CBS 7897 28S rRNA gene, partial sequence from TYPE material | 158 | 158 | 32.00% | 1.00E-35 | 85.00% | NG_058372.1 | |
| 16 | 13 | Phyllozyma coprosmicola CBS 7897 28S rRNA gene, partial sequence from TYPE material | 158 | 158 | 32.00% | 1.00E-35 | 85.00% | NG_058371.1 | |
| 17 | 13 | Phyllozyma subbrunnea CBS 7196 28S rRNA gene, partial sequence from TYPE material | 158 | 158 | 32.00% | 1.00E-35 | 85.00% | NG_057702.1 | |
| 18 | 13 | Minimedusa polyspora CBS 113.16 28S rRNA gene, partial sequence: from TYPE material | 158 | 158 | 33.00% | 1.00E-35 | 84.00% | NG_057640.1 | |
| 19 | 13 | Phyllozyma subbrunnea culture CBS:7196 large subunit ribosomal RNA gene, partial sequence | 158 | 158 | 32.00% | 1.00E-35 | 85.00% | KY108779.1 | |
| 20 | 13 | Phyllozyma linderae culture CBS:7893 large subunit ribosomal RNA gene, partial sequence | 158 | 158 | 32.00% | 1.00E-35 | 85.00% | KY108777.1 | |
| 21 | 13 | Phyllozyma coprosmicola culture CBS:7897 large subunit ribosomal RNA gene, partial sequence | 158 | 158 | 32.00% | 1.00E-35 | 85.00% | KY108776.1 | |
| 22 | 13 | Minimedusa polyspora gene for 28S rRNA, partial sequence, strain: CBS 113.16 | 158 | 158 | 33.00% | 1.00E-35 | 84.00% | AB972779.1 | |
| 23 | 13 | Malassezia equina strain MA 146 26S ribosomal RNA gene, partial sequence | 158 | 158 | 34.00% | 1.00E-35 | 84.00% | AY743621.1 | |
| 24 | 13 | Saccharomyces subbrunneus isolate AF70L-IO 898 28S large subunit ribosomal RNA gene, partial sequence | 158 | 158 | 32.00% | 1.00E-35 | 85.00% | AY745717.1 | |
| 25 | 13 | Phyllozyma subbrunnea strain CBS 7196 26S ribosomal RNA gene, partial sequence | 158 | 158 | 32.00% | 1.00E-35 | 85.00% | AF189973.1 | |
| 26 | 13 | Phyllozyma subbrunnea strain CBS 7893 26S ribosomal RNA gene, partial sequence | 158 | 158 | 32.00% | 1.00E-35 | 85.00% | AF189969.1 | |
| 27 | 13 | Phyllozyma coprosmicola strain CBS 7897 26S ribosomal RNA gene, partial sequence | 158 | 158 | 32.00% | 1.00E-35 | 85.00% | AF189881.1 | |
| 28 | 13 | Sporobolomyces linderae 26S ribosomal RNA gene, partial sequence | 158 | 158 | 32.00% | 1.00E-35 | 85.00% | AF207890.1 | |
| 29 | 29 | Hydnum berkeleyanum voucher KD-MEH 17-035 large subunit ribosomal RNA gene, partial sequence | 156 | 156 | 32.00% | 4.00E-35 | 85.00% | MG272970.1 | |
| 30 | 29 | Geastrum verrucoramulosum INPA 264956 28S rRNA gene, partial sequence, from TYPE material | 156 | 156 | 33.00% | 4.00E-35 | 84.00% | NG_060680.1 | |
| 31 | 29 | Clavulina ossea culture URM:BRA:>889.70 28S rRNA, partial sequence, from TYPE material | 156 | 156 | 32.00% | 4.00E-35 | 84.81% | NG_058957.1 | |
| 32 | 29 | Clavulina ossea voucher URM:BRA:>889.70 large subunit ribosomal RNA gene, partial sequence | 156 | 156 | 32.00% | 4.00E-35 | 84.81% | KX811197.1 | |
| 33 | 29 | Geastrum verrucoramulosum voucher INPA:264656 28S ribosomal RNA gene, partial sequence | 156 | 156 | 33.00% | 4.00E-35 | 84.38% | KX670831.1 | |
| 34 | 29 | Burgella flavoparmeliae strain JL192-01 23S large subunit ribosomal RNA gene, partial sequence | 156 | 156 | 32.00% | 4.00E-35 | 84.81% | DQ915469.1 | |

Fig.15

H9-03-28S_D2R2
Search condition: Limit to sequences from type material

| Sequence number | Number by Max score | Description | Max score | Total score | Query cover | E value | Ident | Accession | |
|---|---|---|---|---|---|---|---|---|---|
| 1 | 1 | Chlorellidium tetrabotrys strain SAG811-1 28S ribosomal RNA gene, partial sequence | 215 | 215 | 48.00% | 6.00E-53 | 84.21% | FJ830891.1 | Yellow-green algae |
| 2 | 2 | Fimicolochytrium jonesii JEL 569 28S rRNA gene, partial sequence; from TYPE material | 206 | 206 | 48.00% | 4.00E-50 | 83.56% | NG_060391.1 | Fungus |
| 3 | 2 | Fimicolochytrium jonesii voucher JEL569 28S large subunit ribosomal RNA gene, partial sequence | 206 | 206 | 48.00% | 4.00E-50 | 83.56% | HQ901661.1 | Fungus |
| 4 | 4 | Geranomyces variabilis voucher MF03 28S large subunit ribosomal RNA gene, partial sequence | 200 | 200 | 48.00% | 2.00E-48 | 83.33% | HQ901692.1 | Fungus |
| 5 | 5 | Thoreauomyces humboldtii JEL 95 28S rRNA gene, partial sequence; from TYPE material | 199 | 199 | 48.00% | 7.00E-48 | 83.19% | NG_059938.1 | Fungus |
| 6 | 5 | Thoreauomyces humboldtii voucher JEL95 28S large subunit ribosomal RNA gene, partial sequence | 199 | 199 | 48.00% | 7.00E-48 | 83.19% | HQ901662.1 | |
| 7 | 5 | Spizellomyces acuminatus 28S ribosomal RNA (LSU) gene, partial sequence | 198 | 198 | 48.00% | 7.00E-48 | 83.11% | JN411010.1 | |
| 8 | 5 | Phlyctochytrium africanum voucher CBS 484.65 28S rRNA gene, partial sequence | 198 | 198 | 48.00% | 7.00E-48 | 83.11% | FJ827693.1 | |
| 9 | 9 | Hobermannella wattica CBS 9496 28S rRNA gene, partial sequence; from TYPE material | 196 | 196 | 48.00% | 2.00E-47 | 82.99% | NG_058307.1 | |
| 10 | 9 | Hobermannella wattica CBS 9496 28S large subunit ribosomal RNA gene, partial sequence | 196 | 196 | 48.00% | 2.00E-47 | 82.89% | KY107814.1 | |
| 11 | 11 | Fimicolochytrium alabamae JEL 538 28S rRNA gene, partial sequence; from TYPE material | 195 | 195 | 48.00% | 2.00E-47 | 82.67% | NG_060390.1 | |
| 12 | 11 | Gorgonomyces haynaldii BAFC ARG 026 28S rRNA gene, partial sequence; from TYPE material | 195 | 195 | 47.00% | 8.00E-47 | 83.11% | HQ901669.1 | |
| 13 | 13 | Gonapodya semisepta voucher BJFC Cui 10222 28S rRNA gene, partial sequence | 193 | 193 | 48.00% | 3.00E-46 | 82.68% | NG_064354.1 | |
| 14 | 14 | Gonapodya sp. GLZ_2014 voucher Cui HQ222 28S large subunit ribosomal RNA gene, partial sequence | 193 | 193 | 48.00% | 3.00E-46 | 82.68% | KF845949.1 | |
| 15 | 14 | Sonoraphlyctis ranzonii 28S rRNA gene, partial sequence; from TYPE material | 193 | 193 | 48.00% | 3.00E-46 | 82.74% | NG_042454.1 | |
| 16 | 14 | Basidiascus undulatus strain CBS 135761 large subunit ribosomal RNA gene, partial sequence | 193 | 193 | 48.00% | 1.00E-46 | 82.46% | MH877552.1 | |
| 17 | 17 | Piskurozyma taiwanensis CBS 9813 28S rRNA gene, partial sequence; from TYPE material | 191 | 191 | 48.00% | 1.00E-45 | 82.46% | NG_056375.1 | |
| 18 | 17 | Goffeauzyma gastrica CBS 2288 28S rRNA gene, partial sequence; from TYPE material | 191 | 191 | 48.00% | 1.00E-45 | 82.46% | NG_058296.1 | |
| 19 | 17 | Goffeauzyma acidituberans CBS 10872 28S rRNA gene, partial sequence; from TYPE material | 191 | 191 | 48.00% | 1.00E-45 | 82.46% | NG_058295.1 | |
| 20 | 17 | Goffeauzyma aeria CBS 7180 large subunit ribosomal RNA gene, partial sequence | 191 | 191 | 48.00% | 1.00E-45 | 82.46% | KY108813.1 | |
| 21 | 17 | Solicoccozyma aeria culture CBS:2288 large subunit ribosomal RNA gene, partial sequence | 191 | 191 | 48.00% | 1.00E-45 | 82.46% | KY109866.1 | |
| 22 | 17 | Piskurozyma taiwanensis culture CBS:9813 large subunit ribosomal RNA gene, partial sequence | 191 | 191 | 48.00% | 1.00E-45 | 82.46% | KY108944.1 | |
| 23 | 17 | Piskurozyma cylindrica culture CBS:9680 large subunit ribosomal RNA gene, partial sequence | 191 | 191 | 48.00% | 1.00E-45 | 82.46% | KY108932.1 | |
| 24 | 17 | Naganishia globosa culture CBS:5106 large subunit ribosomal RNA gene, partial sequence | 191 | 191 | 48.00% | 1.00E-45 | 82.46% | KY108816.1 | |
| 25 | 17 | Naganishia friedmanii culture CBS:7160 large subunit ribosomal RNA gene, partial sequence | 191 | 191 | 48.00% | 1.00E-45 | 82.46% | KY108813.1 | |
| 26 | 17 | Goffeauzyma gastrica culture CBS:2288 large subunit ribosomal RNA gene, partial sequence | 191 | 191 | 48.00% | 1.00E-45 | 82.46% | KY107764.1 | |
| 27 | 17 | Goffeauzyma acidituberans culture CBS:10872 large subunit ribosomal RNA gene, partial sequence | 191 | 191 | 48.00% | 1.00E-45 | 82.46% | KY107733.1 | |
| 28 | 17 | Filobasidium wieringae culture CBS:1937 large subunit ribosomal RNA gene, partial sequence | 191 | 191 | 48.00% | 1.00E-45 | 82.35% | KY107733.1 | |
| 29 | 17 | Filobasidium magnum culture CBS:140 large subunit ribosomal RNA gene, partial sequence | 191 | 191 | 48.00% | 1.00E-45 | 82.35% | KY107722.1 | |
| 30 | 17 | Filobasidium globisporum culture CBS:7642 large subunit ribosomal RNA gene, partial sequence | 191 | 191 | 48.00% | 1.00E-45 | 82.38% | KY107713.1 | |
| 31 | 17 | Filobasidium floriforme culture CBS:6241 large subunit ribosomal RNA gene, partial sequence | 191 | 191 | 48.00% | 1.00E-45 | 82.38% | KY107703.1 | |
| 32 | 17 | Filobasidium wieringae culture CBS:7159 large subunit ribosomal RNA gene, partial sequence | 191 | 191 | 48.00% | 1.00E-45 | 82.46% | KY106981.1 | |
| 33 | 17 | [Cryptococcus] terreicolis culture CBS:7196 large subunit ribosomal RNA gene, partial sequence | 191 | 191 | 48.00% | 1.00E-45 | 82.46% | KY106981.1 | |
| 34 | 17 | [Cryptococcus] allelius var. cooliae culture CBS:5810 large subunit ribosomal RNA gene, partial sequence | 191 | 191 | 48.00% | 1.00E-45 | 82.46% | KY106965.1 | |
| 35 | 17 | [Cryptococcus] allelius var. kuetzingii culture CBS:1926 large subunit ribosomal RNA gene, partial sequence | 191 | 191 | 48.00% | 1.00E-45 | 82.46% | KY106960.1 | |
| 36 | 17 | Gemmibasidium hirsutum DAOM 241869 28S rRNA gene, partial sequence; from TYPE material | 191 | 191 | 48.00% | 1.00E-45 | 82.46% | NG_042695.1 | |
| 37 | 17 | Gemmibasidium donium DAOM 241948 28S rRNA gene, partial sequence; from TYPE material | 191 | 191 | 48.00% | 1.00E-45 | 82.46% | NG_042694.1 | |
| 38 | 17 | Basidioascus magus DAOM 241956 28S rRNA gene, partial sequence; from TYPE material | 191 | 191 | 48.00% | 1.00E-45 | 82.46% | NG_042693.1 | |

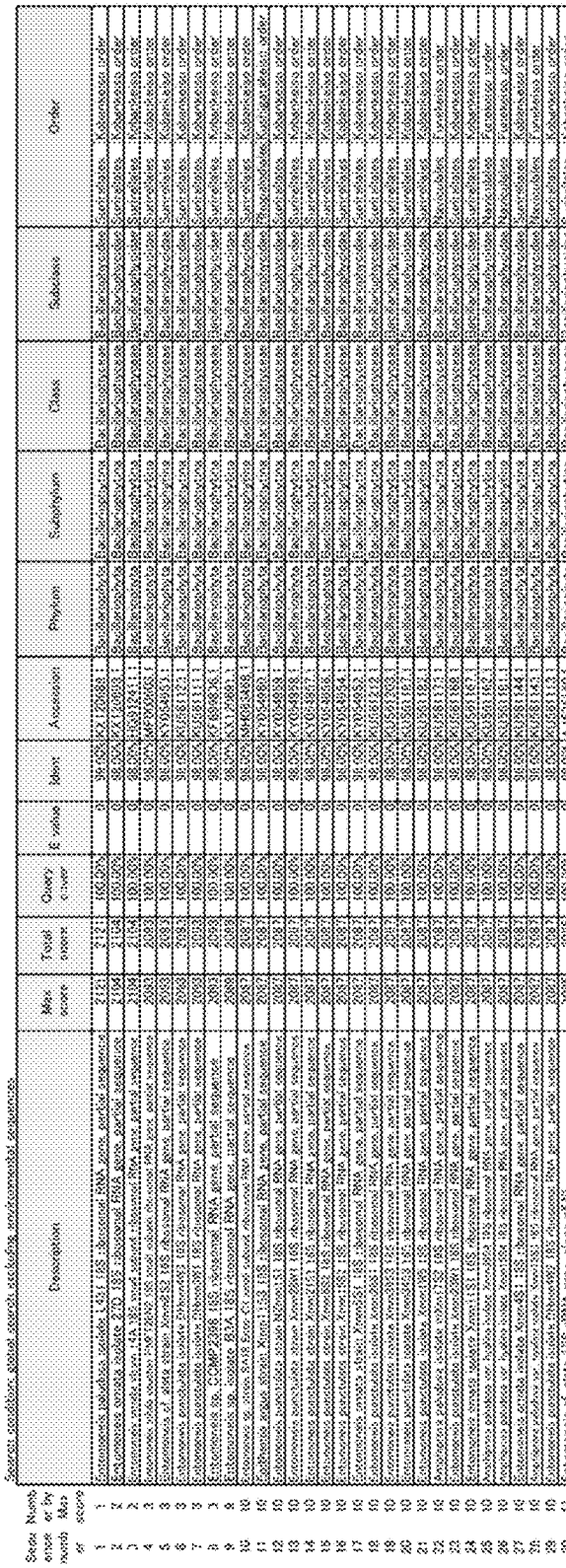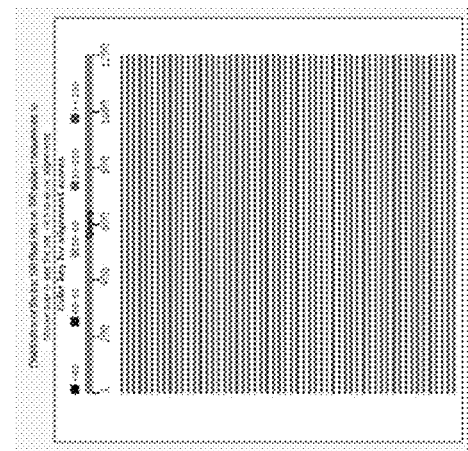
Fig. 16

H9-08-28S D2C2
Search condition: Limit to sequences from type material

| Sequence number | Number by Max score | Description | Max score | Total score | Query cover | E value | Ident | Accession | |
|---|---|---|---|---|---|---|---|---|---|
| 1 | 1 | Nannochloropsis gaditana strain SAG2.98 28S ribosomal RNA gene, partial sequence | 189 | 189 | 40.00% | 3.00E-45 | 86.00% | FJ030680.1 | Nannochloropsis |
| 2 | 2 | Developayella elegans strain CCAP1917/1 28S ribosomal RNA gene, partial sequence | 172 | 172 | 59.00% | 3.00E-40 | 79.00% | FJ030882.1 | Oomycete |
| 3 | 3 | Sporobolomyces dimmenae gene for LSU rRNA, partial sequence, strain: JCM 8762 | 169 | 169 | 26.00% | 4.00E-39 | 93.00% | AB644404.1 | Fungus |
| 4 | 3 | Sporobolomyces coralinus genes for 18S rRNA, ITS1, 5.8S rRNA, ITS2, 28S rRNA, partial and complete sequence | 169 | 169 | 26.00% | 4.00E-39 | 93.00% | AB638335.1 | Fungus |
| 5 | 5 | Paraglomus occultum IRVAM-IA762 28S rRNA gene, partial sequence, from reference material | 167 | 167 | 41.00% | 2.00E-38 | 83.00% | NG_027587.1 | Fungus |
| 6 | 6 | Pseudobaeospora terrestris SFSU DED 8685 28S rRNA gene, partial sequence, from TYPE material | 163 | 163 | 25.00% | 2.00E-37 | 93.00% | NG_060108.1 | |
| 7 | 6 | Pseudobaeospora vesparum voucher DED 8685 28S large subunit ribosomal RNA gene, partial sequence | 163 | 163 | 25.00% | 2.00E-37 | 93.00% | KC464330.1 | |
| 8 | 8 | Afrocastellanos ivoryana OSC 150014 28S rRNA gene, partial sequence, from TYPE material | 158 | 158 | 25.00% | 1.00E-35 | 92.00% | NG_058595.1 | |
| 9 | 8 | Afrocastellanos ivoryana voucher OSC 150014 28S ribosomal RNA gene, partial sequence | 158 | 158 | 25.00% | 1.00E-35 | 92.00% | KX685720.1 | |
| 10 | 8 | Bgcofutus dhakarus HKAS 73785 28S rRNA gene, partial sequence, from TYPE material | 158 | 158 | 25.00% | 1.00E-35 | 92.00% | NG_042663.1 | |
| 11 | 8 | Spongiforma squarepartini voucher LHFB14 28S rRNA gene, partial sequence | 158 | 158 | 25.00% | 1.00E-35 | 92.00% | HQ724309.1 | |
| 12 | 8 | Spongiforma thailandica BBH DED 7873 28S rRNA gene, partial sequence, from TYPE material | 158 | 158 | 25.00% | 1.00E-35 | 92.00% | NG_042464.1 | |
| 13 | 13 | Phyllozyma linderae CBS 7893 28S rRNA gene, partial sequence: from TYPE material | 156 | 156 | 25.00% | 3.00E-35 | 92.00% | NG_058372.1 | |
| 14 | 13 | Phyllozyma coprosmicola CBS 7897 28S rRNA gene, partial sequence: from TYPE material | 156 | 156 | 25.00% | 3.00E-35 | 92.00% | NG_058371.1 | |
| 15 | 13 | Phyllozyma subbrunnea CBS 7196 28S rRNA gene, partial sequence, from TYPE material | 156 | 156 | 25.00% | 3.00E-35 | 92.00% | NG_057732.1 | |
| 16 | 13 | Phyllozyma subbrunnea culture CBS:7196 large subunit ribosomal RNA gene, partial sequence | 156 | 156 | 25.00% | 3.00E-35 | 92.00% | KY108779.1 | |
| 17 | 13 | Phyllozyma linderae culture CBS:7893 large subunit ribosomal RNA gene, partial sequence | 156 | 156 | 25.00% | 3.00E-35 | 92.00% | KY108777.1 | |
| 18 | 13 | Phyllozyma coprosmicola culture CBS:7897 large subunit ribosomal RNA gene, partial sequence | 156 | 156 | 25.00% | 3.00E-35 | 92.00% | KY108776.1 | |
| 19 | 13 | Sporobolomyces subbrunneus isolate AFTOL-ID 848 28S large subunit ribosomal RNA gene, partial sequence | 156 | 156 | 25.00% | 3.00E-35 | 92.00% | AY745177.1 | |
| 20 | 13 | Phyllozyma subbrunnea strain CBS 7196 26S ribosomal RNA gene, partial sequence | 156 | 156 | 25.00% | 3.00E-35 | 92.00% | AF189997.1 | |
| 21 | 13 | Phyllozyma linderae strain CBS 7893 26S rRNA gene, partial sequence | 156 | 156 | 25.00% | 3.00E-35 | 92.00% | AF189989.1 | |
| 22 | 13 | Phyllozyma coprosmicola strain CBS 7897 26S ribosomal RNA gene, partial sequence | 156 | 156 | 25.00% | 3.00E-35 | 92.00% | AF189981.1 | |
| 23 | 13 | Sporobolomyces linderae 26S ribosomal RNA gene, partial sequence | 156 | 156 | 25.00% | 3.00E-35 | 92.00% | AF207890.1 | |
| 24 | 24 | Minimedusa polyspora strain CBS 113.16 28S large subunit ribosomal RNA gene, partial sequence | 154 | 154 | 25.00% | 1.00E-34 | 91.00% | MH866167.1 | |
| 25 | 24 | Hydnum berkeleyanum voucher KO-MEH 17-689 large subunit ribosomal RNA gene, partial sequence | 154 | 154 | 25.00% | 1.00E-34 | 91.00% | MG972970.1 | |
| 26 | 24 | Geastrum verrucoramulosum voucher INPA 264956 28S rRNA gene, partial sequence, from TYPE material | 154 | 154 | 25.00% | 1.00E-34 | 91.00% | NG_060850.1 | |
| 27 | 24 | Malassezia equina CBS 9969 28S rRNA gene, partial sequence | 154 | 154 | 37.00% | 1.00E-34 | 84.00% | NG_060248.1 | |
| 28 | 24 | Claudina ossea URM 89970 28S rRNA gene, partial sequence, from TYPE material | 154 | 154 | 25.00% | 1.00E-34 | 91.00% | NG_058957.1 | |
| 29 | 24 | Arthroderma namibiense KRA F-2012-148 28S rRNA gene, partial sequence, from TYPE material | 154 | 154 | 25.00% | 1.00E-34 | 92.00% | NG_058781.1 | |
| 30 | 24 | Minimedusa polyspora CBS 113.16 28S rRNA gene, partial sequence: from TYPE material | 154 | 154 | 25.00% | 1.00E-34 | 91.00% | NG_057840.1 | |
| 31 | 24 | Claudina ossea culture URM:(BRA)-85970 large subunit ribosomal RNA gene, partial sequence | 154 | 154 | 25.00% | 1.00E-34 | 91.15% | KX811197.1 | |
| 32 | 24 | Geastrum verrucoramulosum voucher INPA:264956 26S ribosomal RNA gene, partial sequence | 154 | 154 | 25.00% | 1.00E-34 | 91.15% | KX670831.1 | |
| 33 | 24 | Arthroderma namibiense voucher KRA large subunit ribosomal RNA gene, partial sequence | 154 | 154 | 25.00% | 1.00E-34 | 91.62% | KT006854.1 | |
| 34 | 24 | Minimedusa polyspora gene for 26S rRNA, partial sequence, strain: CBS 113.16 | 154 | 154 | 25.00% | 1.00E-34 | 91.15% | AB972779.1 | |
| 35 | 24 | Burgella flavogemellata KRA F-2012-01 25S large subunit ribosomal RNA gene, partial sequence | 154 | 154 | 25.00% | 1.00E-34 | 91.15% | DQ915469.1 | |
| 36 | 24 | Malassezia equina strain MA 146 26S ribosomal RNA gene, partial sequence | 154 | 154 | 37.00% | 1.00E-34 | 83.64% | AY743621.1 | |

H9-09-18S
Search condition: Limit to sequences from type material

| Sequence number | Number by Max score | Description | Max score | Total score | Query cover | E value | Ident | Accession | |
|---|---|---|---|---|---|---|---|---|---|
| 1 | 1 | Pedospumella encystans voucher B 40 B9A0671 18S ribosomal RNA gene, partial sequence | 1170 | 1427 | 93.00% | 0 | 89.00% | AY651083.1 | Golden algae |
| 2 | 2 | Spumella vulgaris isolate 199hm 18S ribosomal RNA gene, partial sequence | 1120 | 1370 | 92.00% | 0 | 89.00% | DQ388552.1 | Golden algae |
| 3 | 3 | Streptofilum capillatum strain SAG 2559 small subunit ribosomal RNA gene, partial sequence | 1114 | 1346 | 93.00% | 0 | 88.00% | MG652626.1 | Charophytes |
| 4 | 4 | Fistulifera solaris gene for 18S ribosomal RNA, partial sequence | 1112 | 1350 | 93.00% | 0 | 88.00% | AB769957.1 | Bacillariophyta |
| 5 | 4 | Eustigmatos vischeri isolate SAG 860-1 18S ribosomal RNA gene, complete sequence | 1112 | 1365 | 93.00% | 0 | 88.00% | JX274590.1 | Nannochloropsis |
| 6 | 4 | Eustigmatos polyphem strain SAG 38.84 18S ribosomal RNA gene, complete sequence | 1112 | 1365 | 93.00% | 0 | 88.00% | JX188077.1 | Nannochloropsis |
| 7 | 4 | Vischeria helvetica strain SAG 876-1 18S ribosomal RNA gene, partial sequence | 1112 | 1359 | 93.00% | 0 | 88.00% | JX188080.1 | |
| 8 | 8 | Pseudotetraebriella karsolies strain SAG 2056 18S ribosomal RNA gene, complete sequence | 1109 | 1359 | 93.00% | 0 | 88.00% | EF044311.1 | |
| 9 | 9 | Monodus unipapilla partial 18S rRNA gene, strain SAG 8.83 | 1109 | 1359 | 93.00% | 0 | 88.00% | AM490621.1 | |
| 10 | 10 | Heterococcus fuernrensis partial 18S rRNA gene, strain SAG 835-5 | 1101 | 1352 | 92.00% | 0 | 88.00% | AM490820.1 | |
| 11 | 10 | Heterococcus caespitosus partial 18S rRNA gene, strain SAG 835-2a | 1101 | 1352 | 92.00% | 0 | 88.00% | AF251496.1 | |
| 12 | 10 | Nannochloropsis limnetica strain SAG 18.99 culture collection SAG 18.99 18S ribosomal RNA gene, partial sequence | 1101 | 1346 | 95.00% | 0 | 87.00% | MF038767.1 | |
| 13 | 13 | Glipidopsis heterosphaerica isolate KMD-M-orna4 18S ribosomal RNA gene, partial sequence | 1099 | 1342 | 91.00% | 0 | 88.00% | JQ698935.1 | |
| 14 | 13 | Saitoella complicata strain NRRL Y-17804 18S rRNA gene, partial sequence; from TYPE material | 1088 | 1309 | 93.00% | 0 | 88.00% | NG_013154.1 | |
| 15 | 13 | Saitoella complicata voucher B 40 0040673 18S ribosomal RNA gene, partial sequence | 1088 | 1309 | 93.00% | 0 | 88.00% | AY651074.1 | |
| 16 | 13 | Pelagospumella lacustris voucher B 40 0040673 18S ribosomal RNA gene, partial sequence | 1088 | 1329 | 92.00% | 0 | 88.00% | FJ030892.1 | |
| 17 | 13 | Chlorellidium tetrabotrys strain SAG811-1 18S ribosomal RNA gene, partial sequence | 1086 | 1357 | 92.00% | 0 | 88.00% | D12530.1 | |
| 18 | 18 | Saitoella complicata gene for 18S rRNA | 1086 | 1313 | 93.00% | 0 | 88.00% | D12530.1 | |
| 19 | 19 | Ochromonas danica strain SAG933.7 18S rRNA gene, partial sequence | 1086 | 1315 | 92.00% | 0 | 88.00% | JQ281514.1 | |
| 20 | 20 | Hydrurophytum curvatum SAG 235-1 18S rRNA gene, partial sequence; from reference material | 1077 | 1304 | 93.00% | 0 | 88.00% | NG_017172.1 | |
| 21 | 21 | Micromonas commoda isolate RCC299 18S ribosomal RNA gene, partial sequence; internal transcribed spacer 1, 5.8S ribosomal RNA gene, and internal transcribed spacer 2, complete sequence; and 28S ribosomal RNA gene, partial sequence | 1074 | 1311 | 92.00% | 0 | 88.00% | KU612123.1 | |
| 22 | 21 | Micromonas sp. RCC299 18S ribosomal RNA gene, partial sequence | 1074 | 1311 | 92.00% | 0 | 88.00% | HM191693.1 | |
| 23 | 21 | Micromonas sp. RCC299 chromosome 8, complete sequence | 1074 | 3934 | 92.00% | 0 | 88.00% | CP001575.1 | |
| 24 | 21 | Sphaerosorus compacta partial 18S rRNA gene, strain SAG 53.91 | 1074 | 1329 | 92.00% | 0 | 88.00% | AJ579333.1 | |
| 25 | 25 | Taphrina populina CBS 337.55 18S rRNA gene, partial sequence; from TYPE material | 1070 | 1261 | 92.00% | 0 | 87.00% | NG_062683.1 | |
| 26 | 25 | Taphrina populina gene for 18S rRNA | 1070 | 1261 | 92.00% | 0 | 87.00% | D14165.1 | |
| 27 | 27 | Endogone corticioides gene for 18S ribosomal RNA, partial sequence, specimen voucher A-14652 | 1068 | 1270 | 85.00% | 0 | 88.00% | LC107355.1 | |
| 28 | 27 | Micromonas commoda 18S ribosomal RNA gene, partial sequence | 1068 | 1300 | 92.00% | 0 | 87.00% | KU244632.1 | |
| 29 | 27 | Nannochloropsis oligona 18S rRNA gene, 5.8S rRNA gene, ITS1, 5.8S rRNA gene, ITS2 and 28S rRNA gene (partial), strain SAG 7.96 | 1068 | 1297 | 93.00% | 0 | 87.00% | AM490840.1 | |
| 30 | 27 | Klebsormidium dissectum strain SAG 2155 18S ribosomal RNA gene, partial sequence; internal transcribed spacer 1, 5.8S ribosomal RNA gene, and internal transcribed spacer 2, complete sequence; and 26S ribosomal RNA gene, partial sequence | 1068 | 1291 | 93.00% | 0 | 87.00% | EF372518.1 | |

H9-09-28S_D2R2
Search condition: Limit to sequences from type material

| | Description | Max score | Total score | Query cover | E value | Ident | Accession | |
|---|---|---|---|---|---|---|---|---|
| 1 | Chlorellidium tetrabotrys strain SAG611-1 28S ribosomal RNA gene, partial sequence | 196 | 196 | 50.00% | 2.00E-47 | 82.00% | FJ030881.1 | Yellow-green algae |
| 2 | Cercospora sp. CLZ-2014 voucher Cs 19222 28S large subunit ribosomal RNA gene, partial sequence | 185 | 185 | 50.00% | 4.00E-44 | 81.00% | KF845949.1 | Fungus |
| 3 | Spizellomyces acuminatus 28S ribosomal RNA (LSU) gene, partial sequence | 183 | 183 | 50.00% | 1.00E-43 | 81.00% | JN941010.1 | Fungus |
| 4 | Phlyctochytrium africanum voucher CBS 454.65 28S ribosomal RNA gene, partial sequence | 183 | 183 | 50.00% | 1.00E-43 | 81.00% | FJ827693.1 | Fungus |
| 5 | Fimicolochytrium jonesii JEL 569 28S rRNA gene, partial sequence, from TYPE material | 182 | 182 | 50.00% | 5.00E-43 | 81.00% | NG_060391.1 | Fungus |
| 6 | Geranomyces variabilis voucher MP93 28S large subunit ribosomal RNA gene, partial sequence | 182 | 182 | 50.00% | 5.00E-43 | 81.00% | HQ901692.1 | |
| 7 | Fimicolochytrium jonesii voucher JEL569 28S large subunit ribosomal RNA gene, partial sequence | 182 | 182 | 50.00% | 5.00E-43 | 81.00% | HQ901661.1 | |
| 8 | Thoreauomyces humboldtii JEL 95 28S rRNA gene, partial sequence, from TYPE material | 180 | 180 | 50.00% | 2.00E-42 | 81.00% | NG_059938.1 | |
| 9 | Thoreauomyces humboldtii voucher JEL 95 28S large subunit ribosomal RNA gene, partial sequence | 180 | 180 | 50.00% | 2.00E-42 | 81.00% | HQ901662.1 | |
| 10 | Sonoraphlyctis ranzonii DAOM BR 066 28S rRNA partial sequence from TYPE material | 180 | 180 | 50.00% | 2.00E-42 | 81.00% | NG_042454.1 | |
| 11 | Basidioascus undulatus strain CBS 133783 28S large subunit ribosomal RNA gene, partial sequence | 178 | 178 | 50.00% | 6.00E-42 | 80.00% | MH677552.1 | |
| 12 | Pleurozoma taiwanensis CBS 10872 28S rRNA gene, partial sequence, from TYPE material | 178 | 178 | 50.00% | 6.00E-42 | 80.00% | NG_059375.1 | |
| 13 | Coffeasoyzma acidotolerans CBS:155 large subunit ribosomal RNA gene, partial sequence | 178 | 178 | 50.00% | 6.00E-42 | 80.00% | NG_059295.1 | |
| 14 | Schizococcozyma seria culture CBS:9813 large subunit ribosomal RNA gene, partial sequence | 178 | 178 | 50.00% | 6.00E-42 | 80.00% | KY109666.1 | |
| 15 | Pleurozyma taiwanensis culture CBS:8613 large subunit ribosomal RNA gene, partial sequence | 178 | 178 | 50.00% | 6.00E-42 | 80.00% | KY109334.1 | |
| 16 | Pleurocryptis cylindrica culture CBS:8580 large subunit ribosomal RNA gene, partial sequence | 178 | 178 | 50.00% | 6.00E-42 | 80.00% | KY109932.1 | |
| 17 | Naganishia globosa culture CBS:5106 large subunit ribosomal RNA gene, partial sequence | 178 | 178 | 50.00% | 6.00E-42 | 80.00% | KY108616.1 | |
| 18 | Goffeauzyma friedmannii culture CBS:10872 large subunit ribosomal RNA gene, partial sequence | 178 | 178 | 50.00% | 6.00E-42 | 80.00% | KY108613.1 | |
| 19 | Goffeauzyma acidotolerans culture CBS:10817 large subunit ribosomal RNA gene, partial sequence | 178 | 178 | 50.00% | 6.00E-42 | 80.00% | KY107783.1 | |
| 20 | Filobasidium wieringae culture CBS:1917 large subunit ribosomal RNA gene, partial sequence | 178 | 178 | 50.00% | 6.00E-42 | 80.00% | KY107733.1 | |
| 21 | Filobasidium magnum culture CBS:140 large subunit ribosomal RNA gene, partial sequence | 178 | 178 | 50.00% | 6.00E-42 | 80.00% | KY107722.1 | |
| 22 | Filobasidium globisporum culture CBS:7642 large subunit ribosomal RNA gene, partial sequence | 178 | 178 | 50.00% | 6.00E-42 | 80.00% | KY107713.1 | |
| 23 | Filobasidium floriforme culture CBS:6241 large subunit ribosomal RNA gene, partial sequence | 178 | 178 | 50.00% | 6.00E-42 | 80.00% | KY107703.1 | |
| 24 | Cryptococcus consortionis culture CBS:7189 large subunit ribosomal RNA gene, partial sequence | 178 | 178 | 50.00% | 6.00E-42 | 80.00% | KY106981.1 | |
| 25 | Cryptococcus albidus var. ovalis culture CBS:5810 large subunit ribosomal RNA gene, partial sequence | 178 | 178 | 50.00% | 6.00E-42 | 80.00% | KY106985.1 | |
| 26 | Cryptococcus albidus var. kuetzingii culture CBS:1926 large subunit ribosomal RNA gene, partial sequence | 178 | 178 | 50.00% | 6.00E-42 | 80.00% | KY106980.1 | |
| 27 | Geminibasidium hirsutum DAOM 241969 28S rRNA, partial sequence, from TYPE material | 178 | 178 | 50.00% | 6.00E-42 | 80.00% | NG_042685.1 | |
| 28 | Geminibasidium donsium DAOM 241966 28S rRNA, partial sequence, from TYPE material | 178 | 178 | 50.00% | 6.00E-42 | 80.00% | NG_042684.1 | |
| 29 | Basidioascus magnus DAOM 241843 28S rRNA, partial sequence, from TYPE material | 178 | 178 | 50.00% | 6.00E-42 | 80.00% | NG_042693.1 | |
| 30 | Basidioascus undulatus DAOM 241936 28S rRNA, partial sequence, from TYPE material | 178 | 178 | 50.00% | 6.00E-42 | 80.00% | NG_042692.1 | |

# METHOD FOR PRODUCING 3,5-DIHYDROXY-4-METHOXYBENZYL ALCOHOL FROM PLANKTON

TECHNICAL FIELD

The present invention relates to a producing method for 3,5-dihydroxy-4-methoxysbenzyl alcohol for producing 3,5-dihydroxy-4-methoxybenzyl alcohol as an antioxidant rom plankton.

BACKGROUND ART

The present inventor has already found 3,5-dihydroxy-4-methoxybenzyl alcohol (hereinafter referred to as DHMBA) as a new antioxidant from a heated oyster meat, and succeeded in its synthesis and identification. D-MBA has not been detected from a raw oyster meat.

Here, as ecological features of oyster, it has been generally known that an oyster inhales a large amount of seawater, and takes in plankton as a prey from the inhaled large amount of seawater.

Patent Document 1: JP-A-2016-42825

DISCLOSURE OF THE INVENTION

Problems to be Solved by the Invention

However, the present inventor made a hypothesis that plankton contains DHMBA in the present invention.

Then, when the present inventor collected plankton, filtered them, and measured DHMBA in the plankton, DHMBA was not detected. Next, when the present inventor collected the plankton, filtered them, and heated them, DHMBA was detected. When the present inventor collected the plankton, filtered them, and applied a pressure to them, DHMBA was detected.

In view of this, the present inventor considered that the DHMBA was a useful substance derived from plankton, and reached an invention of a method for producing the DHMBA from the plankton.

Solutions to the Problems

The present invention is a method for producing 3,5-dihydroxy-4-methoxybenzyl alcohol from plankton. The method includes: filtering collected seawater containing the plankton using a filter; taking out a cell content from the plankton remained on the filter; and subsequently heating the cell content thus taken out at a temperature of 60° C. for one hour or more to produce 3,5-dihydroxy-4-methoxybenzyl alcohol from the heated material. The plankton is a diatom belonging to phylum Bacillariophyta, subphylum Bactllariophytina, class Bacillariophyceae, subclass Bacillariophycidae, order Surirellales, family Entomoneidaceae, genus *Entomoneis*.

Alternatively, a method for producing 3,5-dihydroxy-4-methoxybenzyl alcohol from plankton includes: filtering collected seawater containing the plankton using a filter; crushing the plankton remained on the filter with an addition of an extracting solution; and extracting a cell content from the plankton and subsequently performing heating at a temperature of 60° C. for one hour or more to produce 3,5-dihydroxy-4-methoxybenzyl alcohol from the heated material. The plankton is a diatom belonging to phylum Bacillariophyta, subphylum Bacillariophytina, class Bacillariophyceae, subclass Bacillariophycidae, order Surirellales, family Entomoneidaceae, genus *Entomoneis*.

Alternatively, a method for producing 3,5-dihydroxy-4-methoxybenzyl alcohol from plankton includes: filtering collected seawater containing the plankton using a filter; taking out a cell content from the plankton remaining on the filter; and subsequently heating the cell content thus taken out at a temperature of 80° C. for 30 minutes or more to produce 3,5-dihydroxy-4-methoxybenzyl alcohol from the heated material. The plankton is a diatom belonging to phylum Bacillariophyta, subphylum Bacillariophytina, class Bacillariophyceae, subclass Bacillariophycidae, order Surirellales, family Entomoneidaceae, genus *Entomoneis*.

Alternatively, a method for producing 3,5-dihydroxy-4-methoxybenzyl alcohol from plankton includes: filtering collected seawater containing the plankton using a filter: crushing the plankton remained on the filter with an addition of an extracting solution; and extracting a cell content from the plankton and subsequently performing heating at a temperature of 80° C. for 30 minutes or more to produce 3,5-dihydroxy-4-methoxybenzyl alcohol from the heated material. The plankton is a diatom belonging to phylum Bacillariophyta, subphylum Baciliariophytina, class Bacillariophyceae, subclass Bacillariophycidae, order Surirellales, family Entomoneidaceae, genus *Entomoneis*.

Alternatively, a method for producing 3,5dihydroxy-4-methoxybenzyl alcohol from plankton includes: filtering collected seawater containing the plankton using a filter: taking out a cell content from the plankton remained on the filter; and subsequently pressurizing the cell content thus taken out at 2 atmospheres for 30 minutes to produce 3,5-dihydroxy-4-methoxybenzyl alcohol from the pressurized material. The plankton is a diatom belonging to phylum Bacillariophyta, subphylum Bacillariophytina, class Bacillariophyceae, subclass Bacillariophycidae, order Surirellales, family Entomoneidaceae, genus *Entomoneis*.

Alternatively, a method for producing 3,5-dihydroxy-4-methoxybenzyl alcohol from plankton includes: filtering collected seawater containing the plankton using a filter; crushing the plankton remained on the filter with an addition of an extracting solution; and extracting a cell content from the plankton and subsequently performing pressurization at 2 atmospheres for 30 minutes to produce 3,5-dihydroxy-4-methoxybenzyl alcohol from the pressurized material. The plankton is a diatom belonging to phylum Bacillariophyta, subphylum Bacillariophytina, class Bacillariophyceae, subclass Bacillariophycidae, order Surirellales, family Entomoneidaceae, genus *Entomoneis*.

Alternatively, a method for producing 3,5-dihydroxy-4-methoxybenzyl alcohol from plankton includes: filtering collected seawater containing the plankton using a filter: taking out a cell content from the plankton remaining on the filter; and subsequently pressurizing the cell content thus taken out at 2.5 atmospheres for 30 minutes or more to produce 3,5-dihydroxy-4-methoxybenzyl alcohol from the pressurized material. The plankton is a diatom belonging to phylum Bacillariophyta, subphylum Bacillariophytina, class Bacillariophyceae, subclass Bacillariophycidae, order Surirellales, family Entomoneidaceae, genus *Entomoneis*.

Alternatively, a method for producing 3,5-dihydroxy-4-methoxybenzyl alcohol from plankton includes: filtering collected seawater containing the plankton using a filter; crushing the plankton remained on the filter with an addition of an extracting solution; and extracting a cell content from the plankton and subsequently performing pressurization at 2.5 atmospheres for 30 minutes or more to produce 3,5-dihydroxy-1-methoxybenzyl alcohol from the pressurized material. The plankton is a diatom belonging to phylum Bacillariophyta, subphylum Bacillariophytina, class Bacillariophyceae, subclass Bacillanophycidae, order Surirellales, family Entomoneidaceae, genus *Entomoneis*.

Alternatively, a method for producing 3,5-dihydroxy-4-methoxybenzyl alcohol from plankton includes: filtering collected seawater containing the plankton using a filter; taking out a cell content from the plankton remaining on the filter; and subsequently pressurizing the cell content thus taken out at 3 atmospheres for 30 minutes or more to produce 3,5-dihydroxy-4-methoxybenzyl alcohol from the pressurized material. The plankton is a diatom belonging to phylum Bacillariophyta, subphylum Bacillariophytina, class Baacillariophyceae, subclass Bacillariophycidae, order Surirellales, family Entomoneidaceae, genus *Entomoneis*.

Alternatively, a method for producing 3,5-dihydroxy-4-methoxybenzyl alcohol from plankton includes: filtering collected seawater containing the plankton using a filter; crushing the plankton remained on the filter with an addition of an extracting solution; and extracting a cell content from the plankton and subsequently performing pressurization at 3 atmospheres for 30 minutes or more to produce 3,5-dihydroxy-4-methoxybenzyl alcohol from the pressurized material. The plankton is a diatom belonging to phylum Bacillariophyta, subphylum Bacillariophytina, class Bacillariophyceae, subclass Bacillariophycidae, order Surirellales, family Entomoneidaceae, genus *Entomoneis*.

Effects of the Invention

The present invention can provide a method for collecting a seawater containing plankton and producing DHMBA as an antioxidant from the plankton included in the seawater, thus providing an excellent effect.

BRIEF DESCRIPTION OF THE DRAWINGS

FIG. 4 is an explanatory drawing for explaining whether or not DHMBA is produced when plankton existing in a seawater collected in a predetermined sea area of Hiroshima at a predetermined timing is heated.

FIG. 5 an explanatory drawing for explaining whether or not DHMBA is produced when a pressure is applied to plankton existing in a seawater collected in, a predetermined sea area of Hiroshima at a predetermined timing.

FIG. 8 is an explanatory drawing (F) for explaining a result of a search with a search condition limited to sequences from type material.

FIG. 9 is an explanatory drawing (2) for explaining a result of a search with a search condition limited to sequences from type material.

FIG. 12 is an explanatory drawing (5) for explaining a result of a search with a search condition of global search excluding environmental sequences.

FIG. 13 is an explanatory drawing (3) for explaining a result of a search with a search condition limited to sequences from type material.

FIG. 14 is an explanatory drawing (4) for explaining a result of a search with a search condition limited to sequences from type material.

FIG. 15 is an explanatory drawing (5) for explaining a result of a search with a search condition limited to sequences from type material.

FIG. 16 is an explanatory drawing (6) for explaining a result of a search with a search condition of global search excluding environmental sequences, FIG. 17 is an explanatory drawing (7) for explaining a result of a search with a search condition of global search excluding environmental sequences.

FIG. 19 is an explanatory drawing (6) for explaining a result of a search with a search condition limited to sequences from type material.

FIG. 20 is an explanatory drawing (7) for explaining a result of a search with a search condition limited to sequences from type material.

FIG. 21 is an explanatory drawing (8) for explaining, a result of a search with a search condition limited to sequences from type material.

FIG. 22 is an explanatory drawing (9) for explaining a result of a search with a search condition of global search excluding environmental sequences.

FIG. 23 is an explanatory drawing (10) for explaining a result of a search with a search condition of global search excluding environmental sequences.

FIG. 24 is an explanatory drawing (11) for explaining a result of a search with a search condition of global search excluding environmental sequences.

FIG. 25 is an explanatory drawing (9) for explaining a result of a search with a search condition limited to sequences from type material.

FIG. 6 is an explanatory drawing (10) for explaining a result of a search with a search condition limited to sequences from type material.

FIG. 27 is an explanatory drawing (11) for explaining a result of a search with a search condition limited to sequences from type material.

DESCRIPTION OF PREFERRED EMBODIMENTS

First, a seawater was collected in a sea area (for example, sea area of Hiroshima) where an oyster culture was mainly performed at a predetermined timing, the collected seawater was filtered, plankton 1 remaining on a filter used for the filtration were taken out, the plankton 1 was heated or pressurized, and then a search and an analysis of whether DH-MBA was detected or not were performed.

First, the detection of DHMBA by heating will be described.

A seawater was collected in a sea area as a field of oyster culture (for example, sea area of Hiroshima).

Collection of Seawater Containing Plankton

A seawater containing plankton in September is pumped up by a pump or the like in a sea area (for example, sea area of Hiroshima) where an oyster culture is performed.

While the seawater in the sea area of Hiroshima was collected in this embodiment, the seawater is not limited to the seawater of Hiroshima.

For the timing, it is not limited to the seawater in September.

(Filtration of Seawater Containing Plankton)

Figure 1:
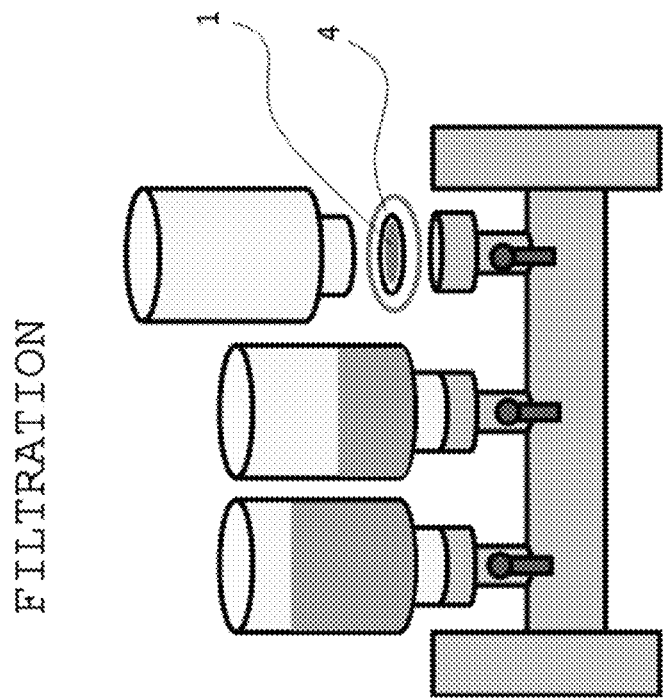
FIG. 1 is a drawing for explaining a filtration of a collected seawater.

After collecting the seawater containing the plankton 1, the seawater is filtered by, for example, a GF/C filter 4 formed of nonwoven fabric or (the like (see FIG. 1).

Here, while the amount of seawater to be filtered is not limited, the seawater was collected by about 3100 liters for each in the sea area of Hiroshima in this time, and filtered.

A large amount of the plankton 1 adhere to the filter after the filtration by the above-described method, and the filter to which the plankton 1 adhere can be kept frozen until the extraction work is performed.

(Ultrasonic Treatment)

Next, for example, the filter to which the plankton 1 adhere is frozen, and the frozen filter is put in a container 5 such as a centrifuge tube, an ultrapure water or the like is added in the container 5, and further, the plankton f is subjected to a sonication by ultrasonic sound wave for about one hour, a ball milling, or the like to break cell walls, thus causing DHMBA and the like to be easily extracted.

(Extraction)

Figure 2:
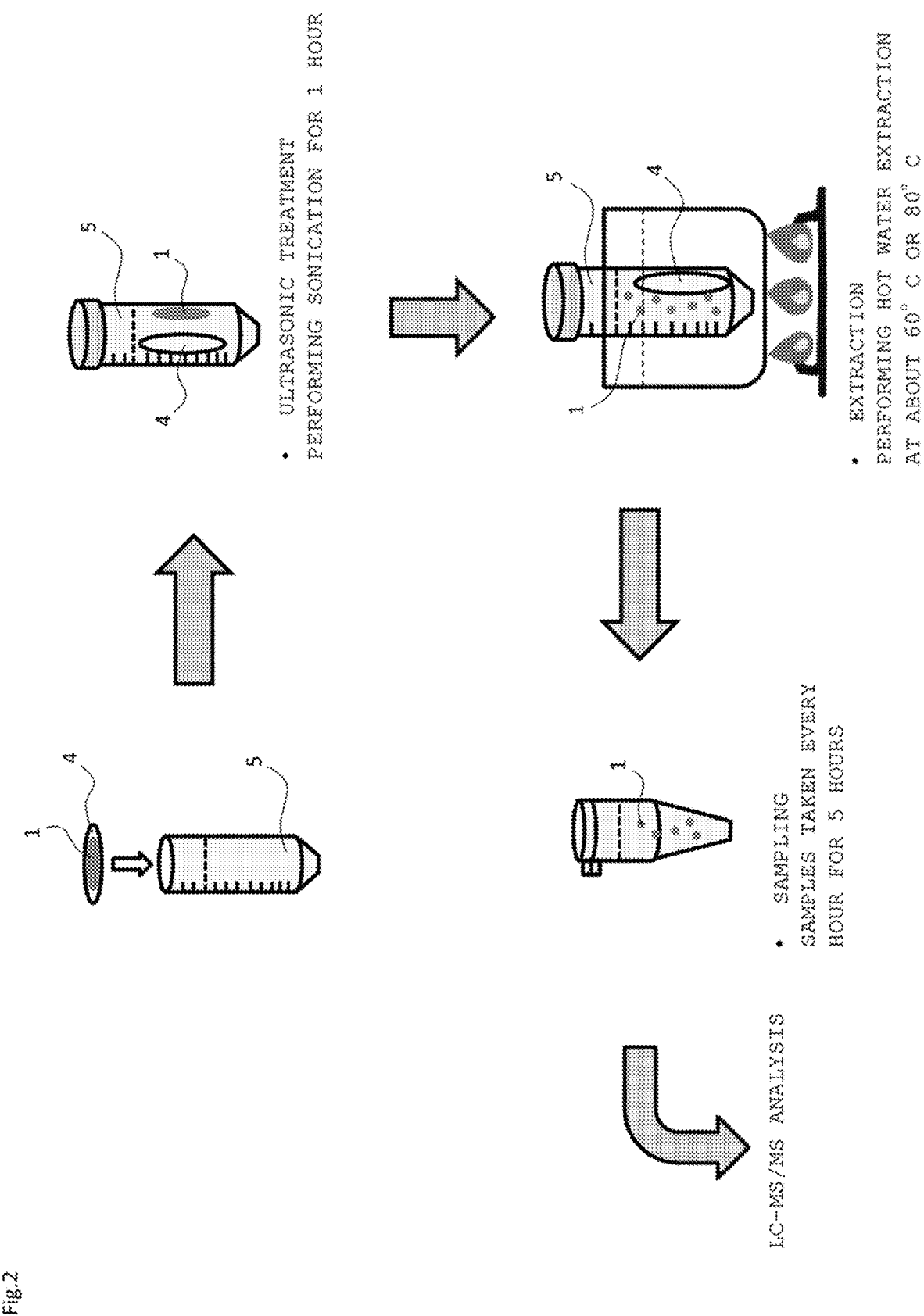
FIG. 2 is a drawing for explaining a sonication of plankton remaining on a filter used for the filtration and a subsequent heating extraction of DHMBA.

After breaking the cells of the plankton 1 by the method such as the sonication, heating is performed to take out contents of the cells. That is, the plankton and the like are subjected to a hot water extraction at about 60° C. or about 80C or the like (see FIG. 2).

Here, because of the heating by hot water-extraction, the plankton 1 in the container 5 is not directly heated. That is, a heated hot water is reserved in a beaker or the like, and the container 5 is put in the hot water, thereby performing what is called indirect heating. This provides an advantage of a stable heating extraction by the heating at a constant temperature or the like.

(Sampling)

Then, for the hot water extraction, sampling was performed at each of 30 minutes, one hour, two hours, three hours four hours, and five hours.

(Analysis of Useful Substance)

The concentration of DHMBA of the sampled plankton 1 was measured by LC-MS/MS.

(Result of Extraction Experiment by Hot Water Extraction Performed at about 60° C.)

DHMBA was not detected in the plankton before heating, and after 30 minutes and after five hours from the hot water extraction.

However, it was confirmed that DHMBA was detected by an extraction amount of 0.0053 (ng/L) after the heating, that is, after one hour from the hot water extraction. It was confirmed that DHMBA was detected by the extraction amount of 0.0064 (ng/L) after two hours from the hot water extraction, and DHMBA was detected by the extraction amount of 0.0059 (ng/L) after three hours from the hot water extraction. Furthermore, it was confirmed that DHMBA was detected by the extraction amount of 0.0063 (ng/L) after four hours from the hot water extraction (see FIG. 4).

(Result of Extraction Experiment by Hot Water Extraction Performed at about 80° C.)

DHMBA was not detected in the plankton before heating and after two hours from the hot water extraction.

However, it was confirmed that DHMBA was detected by the extraction amount of 0.0035 (ng/L) after the heating, that is, after 30 minutes from the hot water extraction, and DHMBA was detected by the extraction amount of 0.0053 (ng/L) after one hour from the hot water extraction. It was confirmed that DHMBA was detected by the extraction amount of 0.0035 (ng/L) after three hours from the hot water extraction, and DHMBA was detected by the extraction amount of 0.0045 (ng/L) after four hours from the hot water extraction. Furthermore, it was confirmed that DHMBA was detected by the extraction amount of 0.0036 (ng/L after five hours from the hot water extraction (see FIG. 4).

Note that, the heating period is not limited to a period until the elapse of one hour. There is a possibility that DHMBA is detected after the heating period shorter than ore hour.

In any case, it was found that while DHMBA was not detected in plankton when the plankton was not heated, DHMBA was promptly detected in the heated plankton when the plankton was heated.

Next, the detection of DHMBA by pressurizing will be described.

First, a seawater was collected in a sea area as a field of oyster culture (for example sea area of Hiroshima).

(Collection of Seawater Containing Plankton)

A seawater in a predetermined timing in a sea area (for example, sea area of Hiroshima) where an oyster culture is performed, that is, a seawater containing plankton in September 2019 in a sea area of Hiroshima prefecture is pumped up by a pump or the like.

While the seawater in the sea area of Hiroshima was collected in this embodiment, the seawater is not limited to the seawater of Hiroshima. For the timing, it is not limited to the seawater in September.

(Filtration of Seawater Containing Plankton)

After collecting the seawater containing the plankton 1, the seawater is filtered by, for example, a GF/C filter 4 formed of a nonwoven fabric or the like (see FIG. 1).

Here, while the amount of seawater to be filtered is not limited, the seawater was collected by about 3100 liters in the sea area of Hiroshima in this time, and filtered.

A large amount of the plankton 1 adhere to the filter after the filtration by the above-described method, and the filter to which the plankton 1 adhere can be kept frozen until the extraction work is performed.

(Ultrasonic Treatment)

Next, for example, the filter to which the plankton 1 adhere is frozen, and the frozen filter is put in a container 5 such as a centrifuge tube, an ultrapure water or the like is added in the container 5, and further, the plankton 1 is subjected to a sonication by ultrasonic sound wave for about one hour, a ball milling, or the like to break cell walls, thus causing DHMBA and the like to be easily extracted.

(Extraction)

Figure 3:
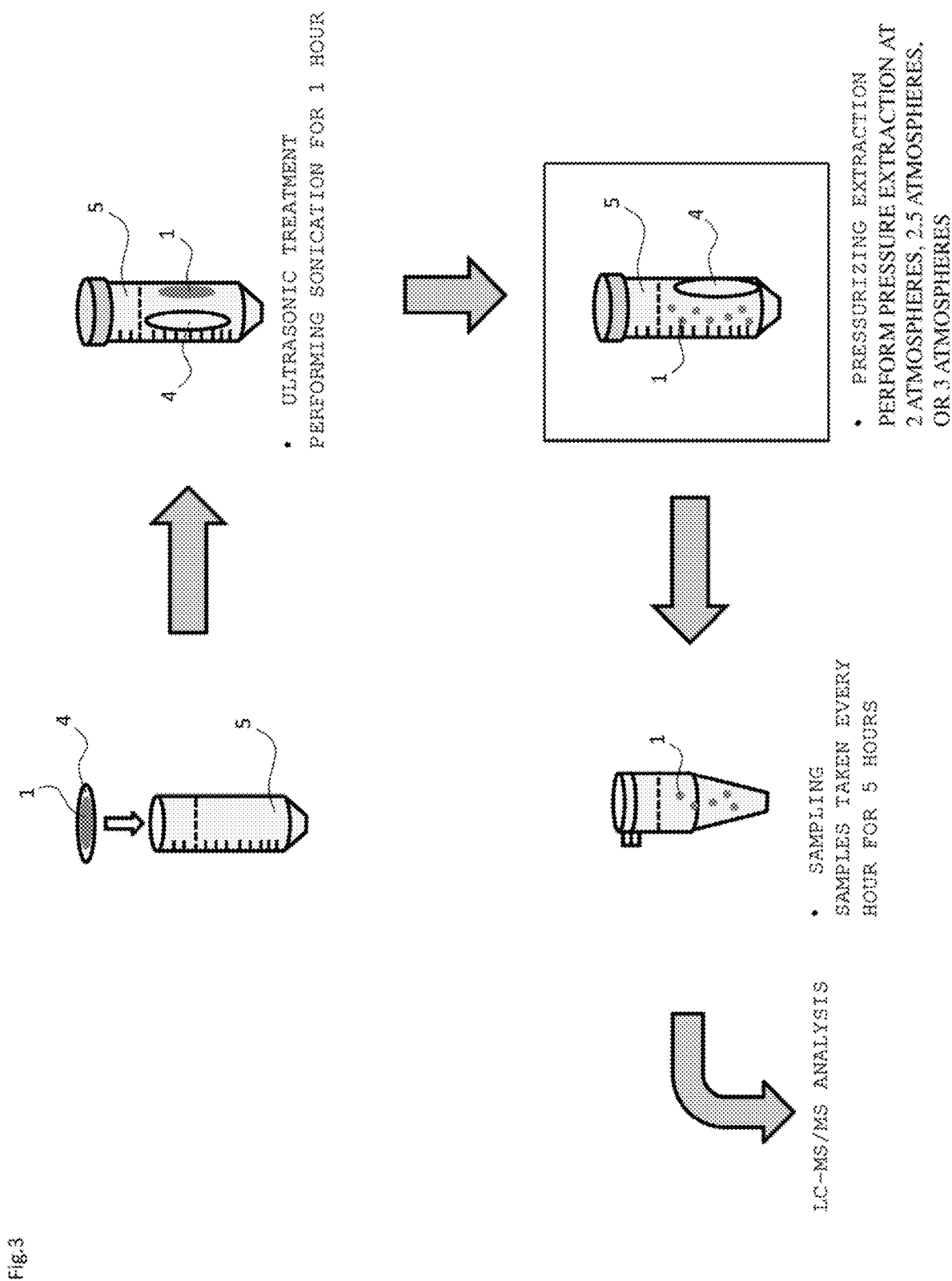
FIG. 3 is a drawing for explaining a sonication of plankton remaining on a filter used for the filtration and a subsequent pressure extraction of DHMBA.

Then, after breaking the cells of the plankton 1 by the method such as the sonication, a pressure is applied to them to extract contents of the cells. That is, the plankton and the like are pressurized to about 2 atmospheres, about 2.5 atmospheres, or about 3 atmospheres, thus performing the extraction (see FIG. 3).

Here, the pressurizing method is not limited. The pressurization may be performed using an autoclave as a general method. The pressurization may be performed by another method.

(Sampling)

Then, for the pressure extraction, sampling was performed at each of 30 minutes, one hour, three hours, and five hours.

(Analysis of Useful Substance)

The concentration of DHMBA of the sampled plankton 1 was measured by LC-MS/MS.

(Result of Extraction Experiment by Pressurization to About 2 Atmospheres)

FIG. 5 illustrates the detection result of DHMBA by the sampling in the sea area of Hiroshima.

FIG. 5 illustrates the change in the extraction amount of DHMBA for each time DHMBA was not detected in the plankton before the pressurization. It was confirmed that DHMBA was detected by the extraction amount of 0.0125 (ng/L) after the pressurization at 2 atmospheres, that is, after the pressurization at 2 atmospheres for 30 minutes.

(Result of Extraction Experiment by Pressurization to About 2.5 Atmospheres)

DHMBA was not detected in the plankton before the pressurization (see FIG. 5) It was confirmed that DHMBA was detected by the extraction amount of 0.197 (ng/L) after the pressurization at 2.5 atmospheres, that is, after the pressurization at 2.5 atmospheres for 30 minutes, and DHMBA was detected by the extraction mount of 0.355 (ng/L) after the pressurization for one hour. It was confirmed that DHMBA was detected by the extraction amount of 0.483 (ng/L) after the pressurization at 2.5 atmospheres for three hours, and DHMBA was detected by the extraction amount of 0,683 (ng/L) after the pressurization at 2.5 atmospheres for five hours (see FIG. 5).

(Result of Extraction Experiment by Pressurization to About 3 Atmospheres)

DHMBA was not detected in the plankton before the pressurization (see FIG. 5) It was confirmed that DHMBA was detected by the extraction amount of 0.282 (ng/L) after the pressurization at 3 atmospheres, that is, after the pressurization at 3 atmospheres for 30 minutes, and DHMBA was detected by the extraction amount of 0.938 (ng/L) after the pressurization for one hour. It was confirmed that DHMBA was detected by the extraction amount of 1.925 (ng/L) after the pressurization at 3 atmospheres for three hours, and DH MBA was detected by the extraction amount of 1,341 (ng/L) after the pressurization at 3 atmospheres for five hours (see FIG. 5).

In any case, it was found that while DHMBA was not detected in plankton when the plankton was not pressurized, DHMBA was promptly detected in the pressurized plankton when the plankton was pressurized.

(Identification of Plankton 1 in Which DHMBA Can Be Detected)

Many kinds of the plankton 1 exist in the seawater, and it has been unknown what kind of the plankton 1 DHMBA is detected in. Therefore, the present inventor decided to identify the plankton 1 in which DHMBA was detected.

The present inventor collected the seawater as described above, and collected the plankton 1 in the seawater.

About 200 kinds were selected from the collected large number of kinds of the plankton 1, and the about 200 kinds of the plankton 1 were each cultured.

Then, the above-described extraction process of DHMBA was performed for each of the about 200 kinds of the cultured plankton. That is, the ultrasonic treatment, the extraction process by heating or pressurizing, and the like were performed.

Consequently, the plankton 1 in which DHMBA was detected were four strains of microalgae. By the observation of the four strains of microalgae based on morphology in detail, they were identified as diatoms.

The diatoms are most abundant in phytoplankton, and many kinds of diatoms exist.

When the present inventor observed the morphology of the four strains of microalgae in which DHMBA was detected in detail by a microscope, the four strains were all diatoms. Here, the magnification of the used microscope is 1.000 times (Eyepiece: 10 Times, Objective Lens: 100 Times)

The four strains of microalgae, that is, diatoms are families of marine diatoms widely distributed in seawater of hays, and known as diatoms producing abundant unsaturated fatty acids. They are also known as super planktonic diatoms.

Next, the present inventor performed a DNA analysis of the four strains of microalgae, that is, diatoms, and intended to further specifically identify the diatoms. The DNA analysis is performed to obtain which class in classification the diatoms belong to, and the class in classification is classified into "phylum," "subphylum," "class," "subclass" "order," "family" "genus," and "species," In the order from the "phylum" toward the "species," the classification levels become more specific.

The following describes the process of the DNA analysis. Classification of Diatom (Strain H-7-09) in Which DHMBA Is Detected It seems a diatom of subclass Bacillariophycidae. However, classification was not made at the level of "order" or below.

(Method)

Performing megaBLAST search with Genbank (NCBI, NH1)

Figure 6:
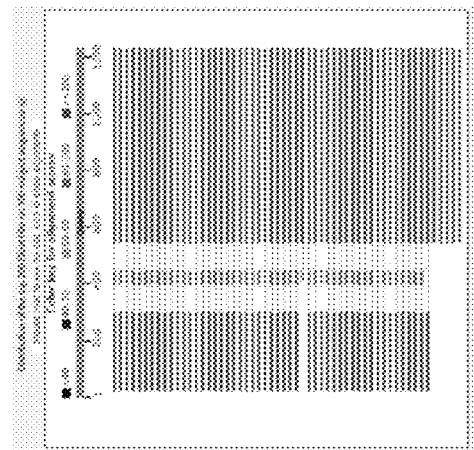
FIG. 6 is an explanatory drawing (1) for explaining a result of a search with a search condition of global search excluding environmental sequences.
Figure 7:
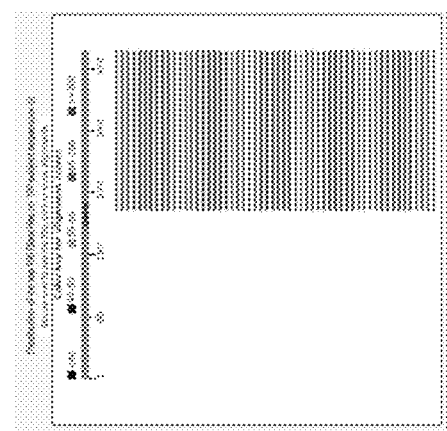
FIG. 7 is an explanatory drawing (2) for explaining a result of a search with a search condition of global search excluding environmental sequences.

Search Condition (1) global search excluding environmental sequences (FIG. 6, FIG. 7)

The examination is performed based on this result.

Search Condition (2) Search limited to sequences from type material (FIG. 8, FIG. 9)

Since the information amount of sequence data of comparison targets were insufficient, the examination based on this result is not performed.

| Site | Sequence name | Base sequence length used for analysis | Sequence assembly | Blast analysis result |
|---|---|---|---|---|
| 18S | H7-09-18S | 1223 bp | Performed | FIG. 6 |
| 28S | H7-09-28S-D2R2 | 474 bp | Not performed | FIG. 7 |

(megaBLAST Search Result)

18S

The homology with the sequence of Humidophila schmassmannii isolate HYU-D030 strain was approximately 96.2%.

The homology is low at approximately 96%.

However, in consideration of sequences hit in the second and subsequent orders, it is supposed to be a diatom of class Bacillariophyceae, subclass Bacillariophycidae.

Sequence of 28S D2R2

The homology with the sequence of Pseudo-nitzschia multistriata strain HAB-132 strain was approximately 96.1%.

The homology is low at approximately 96%. Since the sequence is short, and both the score and the cover rate are low, the degree of reliability on the classification result is low compared with the result of 18S.

However, it is consistent with the possibility of being a diatom of subclass Bacillariophycidae supposed from the result of 18S.

(Classification Result)

They are considered to be diatoms of phylum Bacillariophyta, subphylum Bacillariophytina, class Bacillariophyceae, subclass Bacillariophycidae.

However, classification cannot be made at the level of "order" or below.

Classification of Diatom (Strain H-9-05) in Which DHMBA was Detected

It seems a diatom belonging to phylum Bacillariophyta, subphylum Bacillariophytina, class Bacillariophyceae, subclass Bacillanophycidae, order Surirellales, family Entomoneidaceae, genus *Entomoneis*.

However, classification was not made at the level of "species."

(Method)

Performing megaBLAST search with Genbank (NCBI, NH1)

Figure 10:
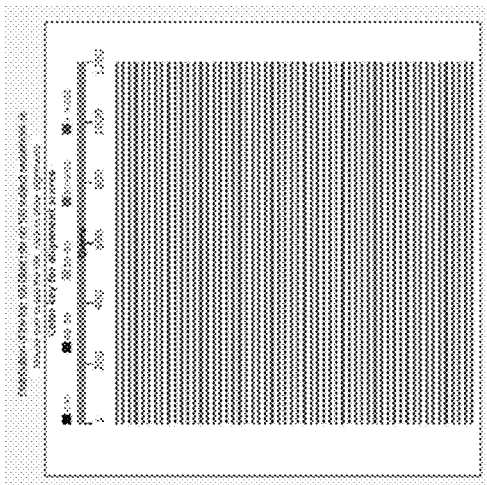
FIG. 10 is an explanatory drawing (3) for explaining a result of a search with a search condition of global search excluding environmental sequences.
Figure 11:
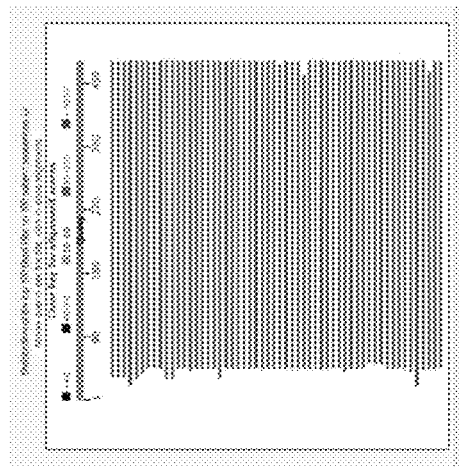
FIG. 11 is an explanatory drawing (4) for explaining a result of a search with a search condition of global search excluding environmental sequences.
Figure 12:
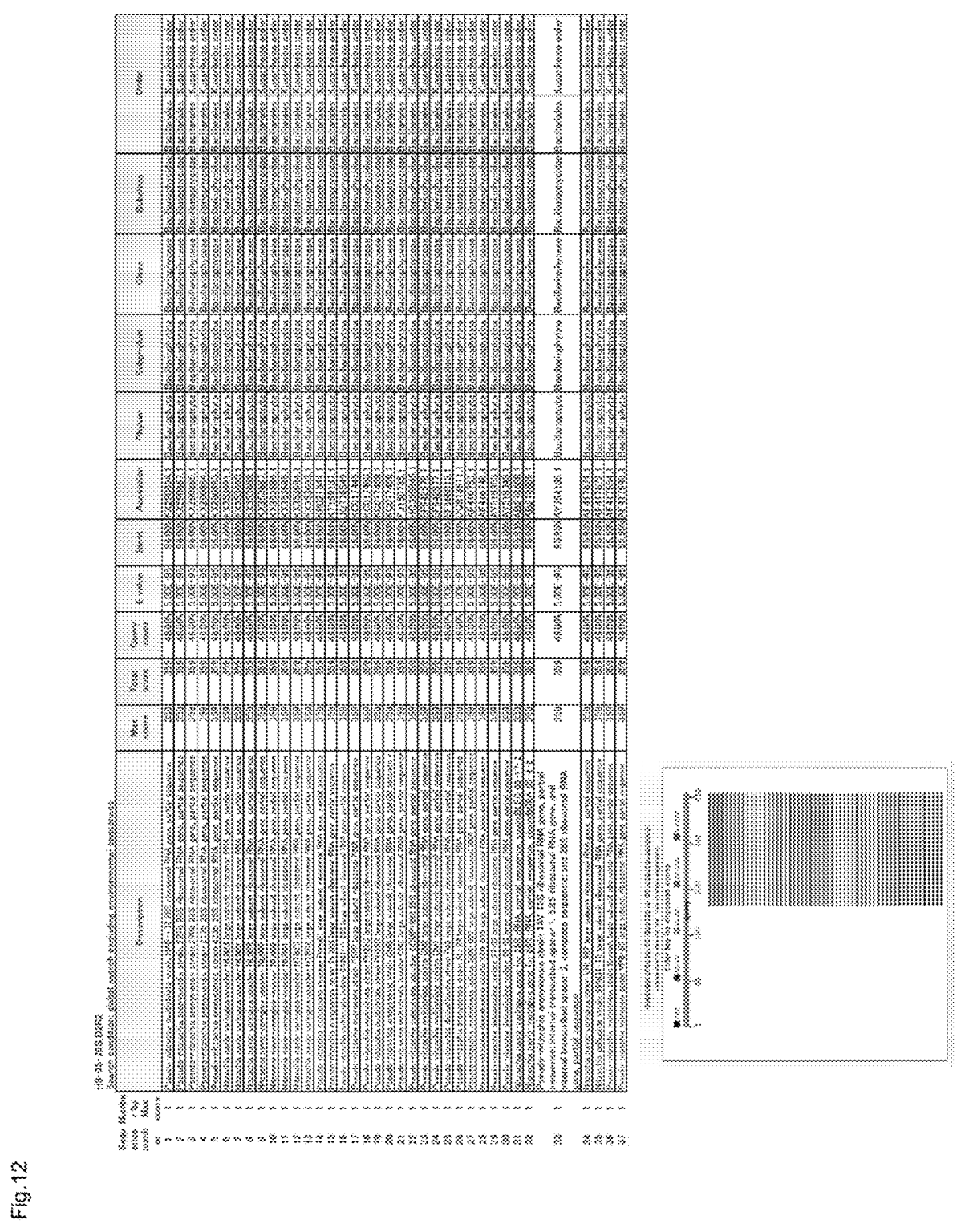

Search Condition (1) global search excluding the environmental sequences (FIG. 10, FIG. 11, FIG. 12)

The examination is performed based on this result.

Search Condition (2) Search limited to sequences from type material (FIG. 11, FIG. 12, FIG. 13)

Since the information amount of sequence data of comparison targets were insufficient, the examination based on this result is not performed.

| Site | Sequence name | Base sequence length used for analysis | Sequence assembly | Base analysis result |
|---|---|---|---|---|
| 18S | H9-05-18S | 1204 bp | Performed | FIG. 10 |
| 28S | H9-05-28S-D2C2 | 480 bp | Not performed | FIG. 11 |
| 28S | H9-05-28S-02R2 | 458 bp | Not performed | FIG. 12 |

(megaBLAST Search Result)

18S

The homology with the sequence of *Entomoneis paludosa* L431 strain was

While the homology is slightly low at 98%, in consideration that the second and subsequent orders hit the genus *Entomoneis*, it is supposed to be a diatom belonging to phylum Bacillariophyta, subphylum Bacillariophytina, class Bacillariophyceae, subclass Bacillariophycidae, order Surirellales, family Entomoneidaceae, genus *Entomoneis*.

Sequence of 28S D2C2

The homology with the sequence of *Entomoneis ornata* 27D strain was 92%.

Since the homology is considerably low at 92%, it is not very useful as a reference. Since the sequence is short, and both the score and the cover rate are low, the degree of reliability on the classification result is considerably low compared with the result of 18S.

However, it is consistent with the possibility of being a diatom of genus *Entomoneis* supposed from the result of 18S.

Sequence of 28S D2R2

The homology with the sequence of Pseudo-nitzschia multistriata HAB-132 strain was 96%.

Since the homology is low at 96%, it is not very useful as a reference. Since the sequence is short, and the score and the cover rate are low compared with D2C2, the degree of reliability on the classification result is considerably low.

However, it is consistent with the possibility of being a diatom of subclass Bacillariophycidae supposed from the result of 18S.

(Classification Result)

They are considered to be diatoms of phylum Bacillariophyta, subphylum Bacillariophytina, class Bacillariophyceae, subclass Bacillariophycidae, order Surirellales, family Entomoneidaceae, genus *Entomoneis*.

However, classification was not made at the level of "species."

Classification of Diatom (Strain H-9-06) in Which DHMBA IS Detected

It seems a diatom belonging to phylum Bacillariophyta, subphylum Bacillariophytina, class Bacillariophyceae, subclass Bacillariophycidae, order Surirellales, family Entomoneidaceae, genus *Entomoneis*.

However, classification was not made at the level of "species".

(Method) Performing megaBLAST search with Genbank (NCBI, NH1)

Figure 17:
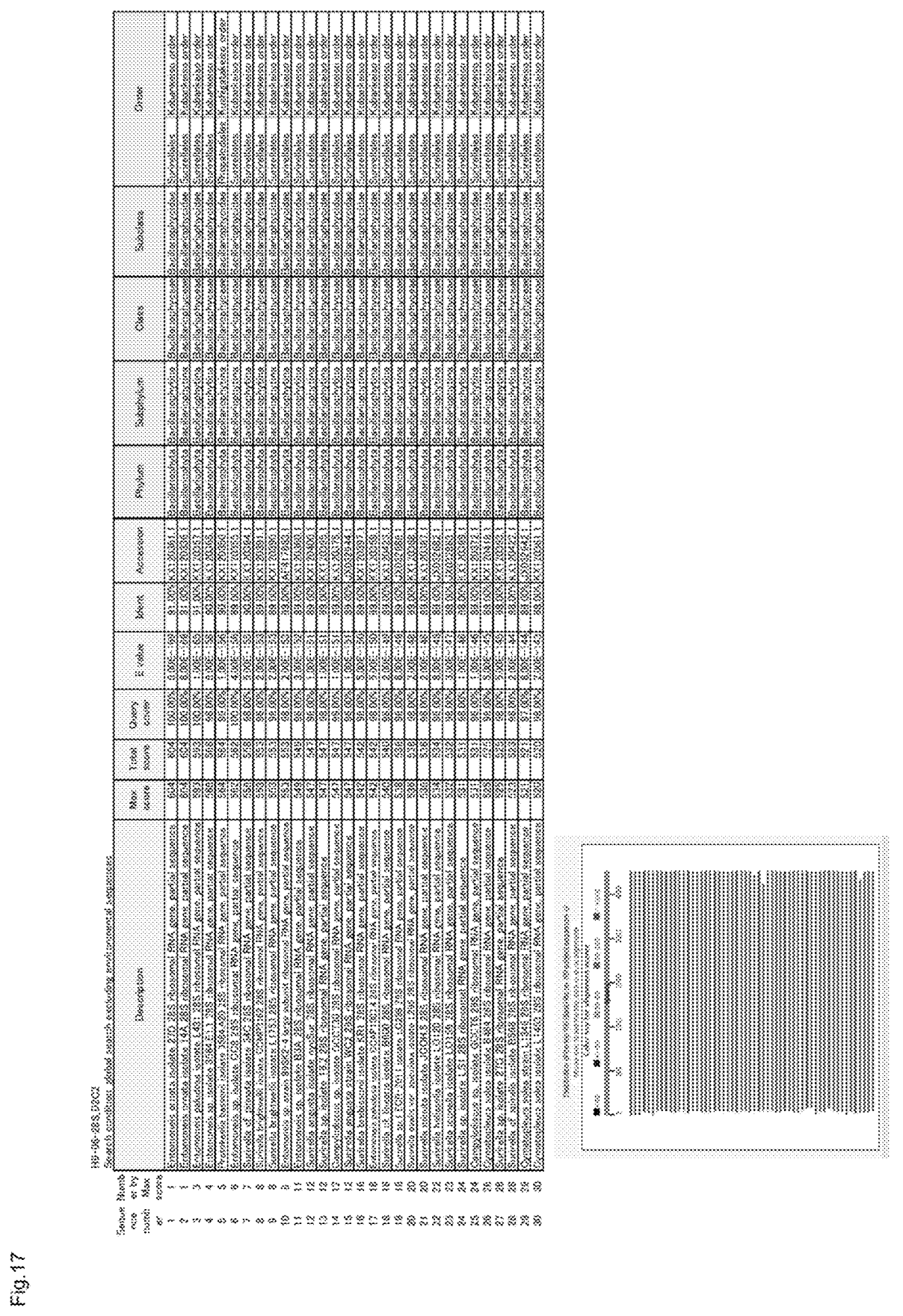
Figure 18:
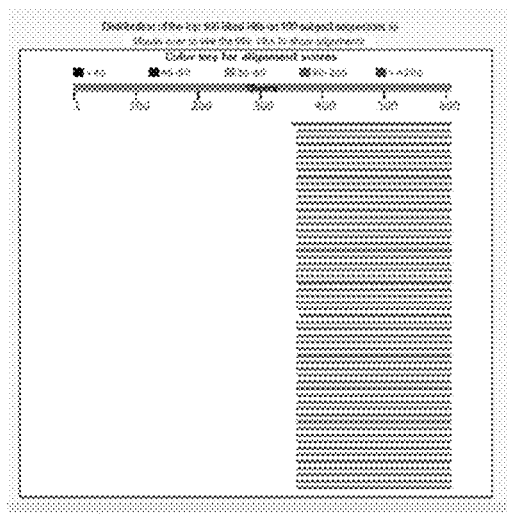
FIG. 18 is an explanatory drawing (8) for explaining a result of a search with a search condition of global search excluding environmental sequences.

Search Condition (1) global search excluding the environmental sequences (FIG. 16, FIG. 17, FIG. 18)

The examination is performed based on this result.

Figure 19:
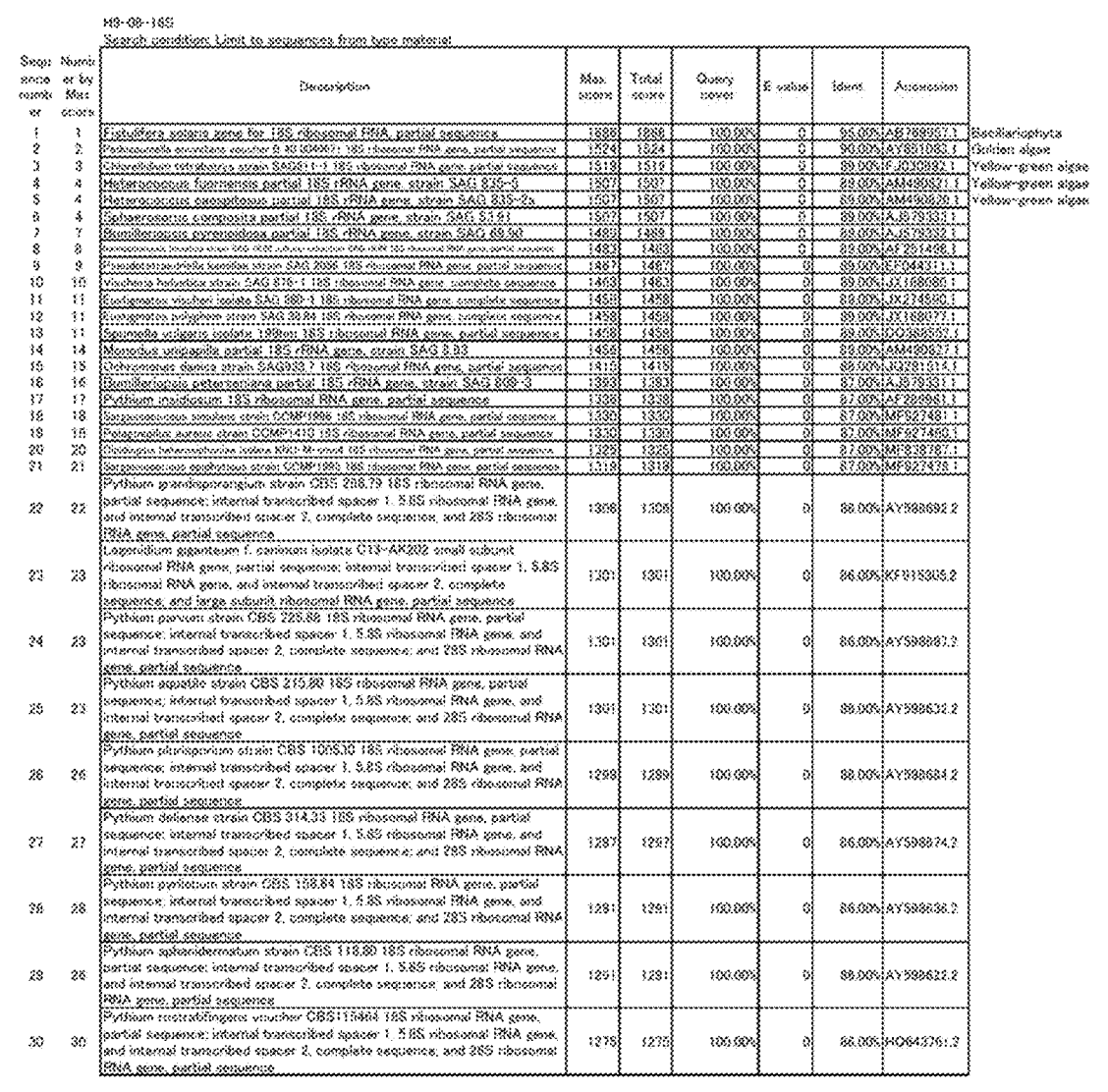
Figure 21:
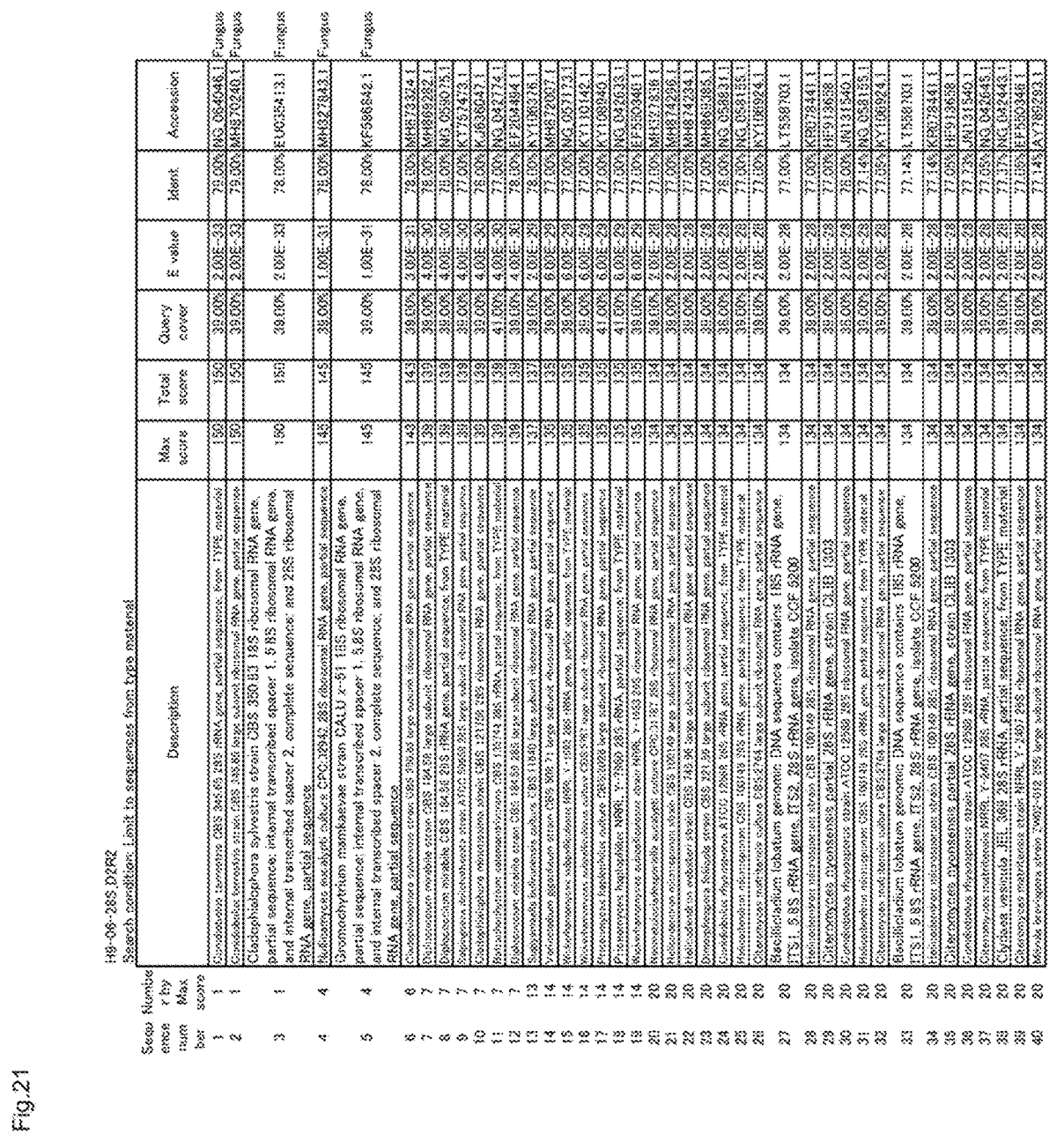

Search Condition (2) Search limited to sequences from type material (FIG. 19, FIG. 20, FIG. 21)

Since the information amount of sequence data of comparison targets were insufficient, the examination based on this result is not performed.

| Site | Sequence name | Base sequence length used for analysis | Sequence assembly | Blast analysis result |
|---|---|---|---|---|
| 18S | H9-06-18S | 1204 bp | Performed | FIG. 16 |
| 28S | H9-06-28S-D2C2 | 440 bp | Not performed | FIG. 17 |
| 28S | H9-06-28S-D2R2 | 609 bp | Not performed | FIG. 18 |

(megaBLAST Search Result)

18S

The homology with the sequence of *Entomoneis paludosa* L431 strain was

In consideration that the homology is 99%, and the second and subsequent orders hit the genus *Entomoneis*, it is supposed to be a diatom belonging to phylum Bacillariophyta, subphylum Bacillariophytina, class Bacillariophyceae, subclass Bacillariophycidae, order Surirellales, family Entomoneidaceae, genus *Entomoneis*.

Sequence of 28S D2C2

The homology with the sequence of *Entomoneis ornata* 27D strain was 91%,

Since the homology is considerably low at 91%, it is not very useful as a reference. Since the sequence is short, and the score is low, the degree of reliability on the classification result is considerably low compared with the result of 18S.

However, it is consistent with the possibility of being a diatom of genus *Entomoneis* supposed from the result of 18S.

Sequence of 28S D2R2

The homology with Vannella septentrionalis (ameba) was 88%.

The homology with fungi forming arbuscular mycorrhiza was 79% or less.

The homology is less than 90%. Since the sequence is short, and the score and the cover rate are low compared with D2C2, the degree of reliability on the classification result is considerably low.

Figure 26:
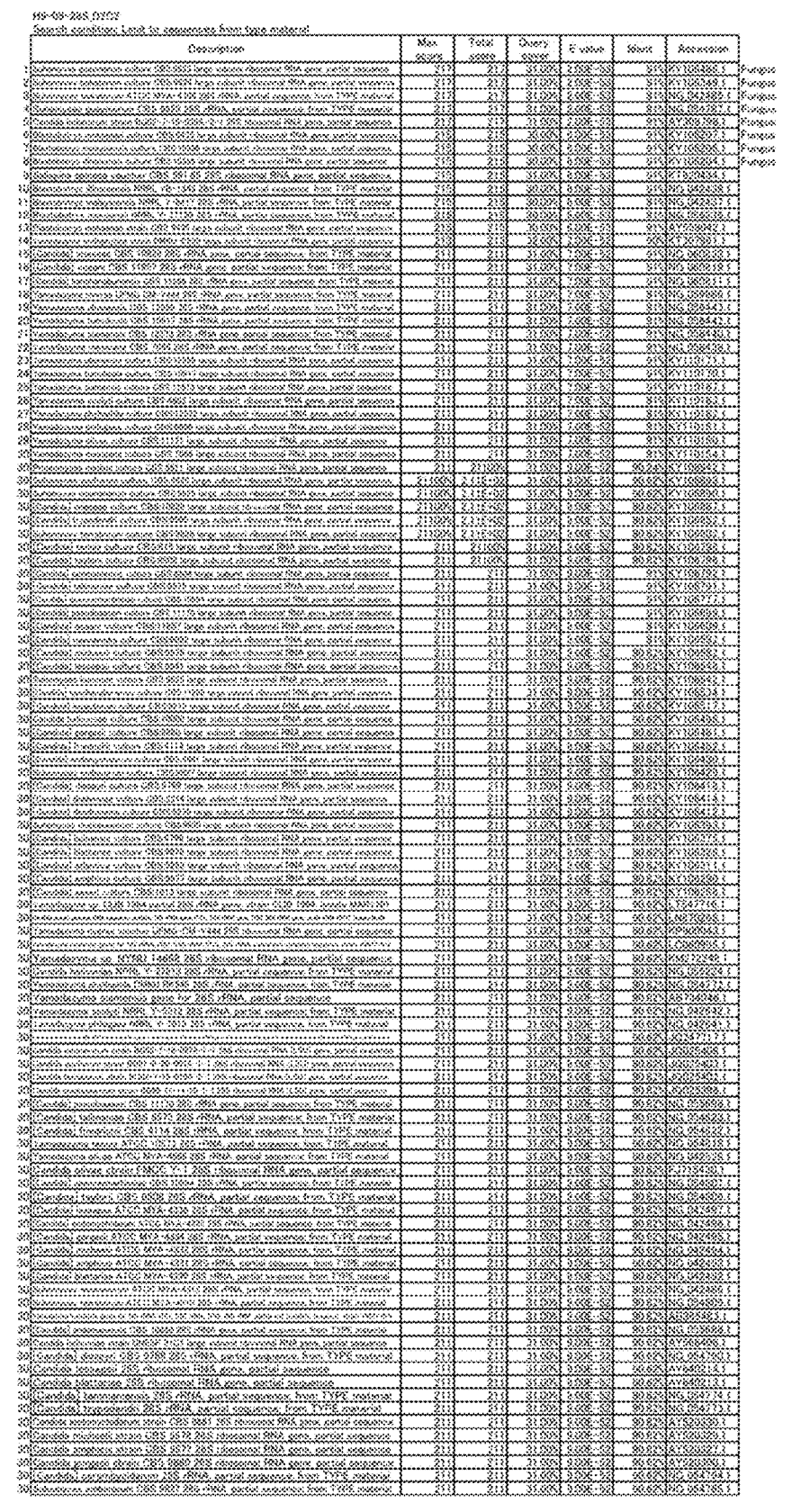

Therefore, it is excluded from this examination on the classification.
(Classification Result)
They are considered to be diatoms of phylum Bacillariophyta, subphylum Bacillariophytina, class Bacillariophyceae, subclass Bacillanophycidae, order Surirellales, family Entomoneidaceae, genus *Entomoneis*.
Strain H-9-09 Classification
Undetermined
(Method) Performing megaBLAST search with Genbank (NCBI, NH1)
Search Condition (1) global search excluding the environmental sequences (FIG. 22, FIG. 23, FIG. 24)
The examination is performed based on this result.
Search Condition (2) search limited to sequences from type material (FIG. 25, FIG. 26, FIG. 27)
Since the information amount of sequence data of comparison targets were insufficient, the examination based on this result is not performed.

Figure 22:
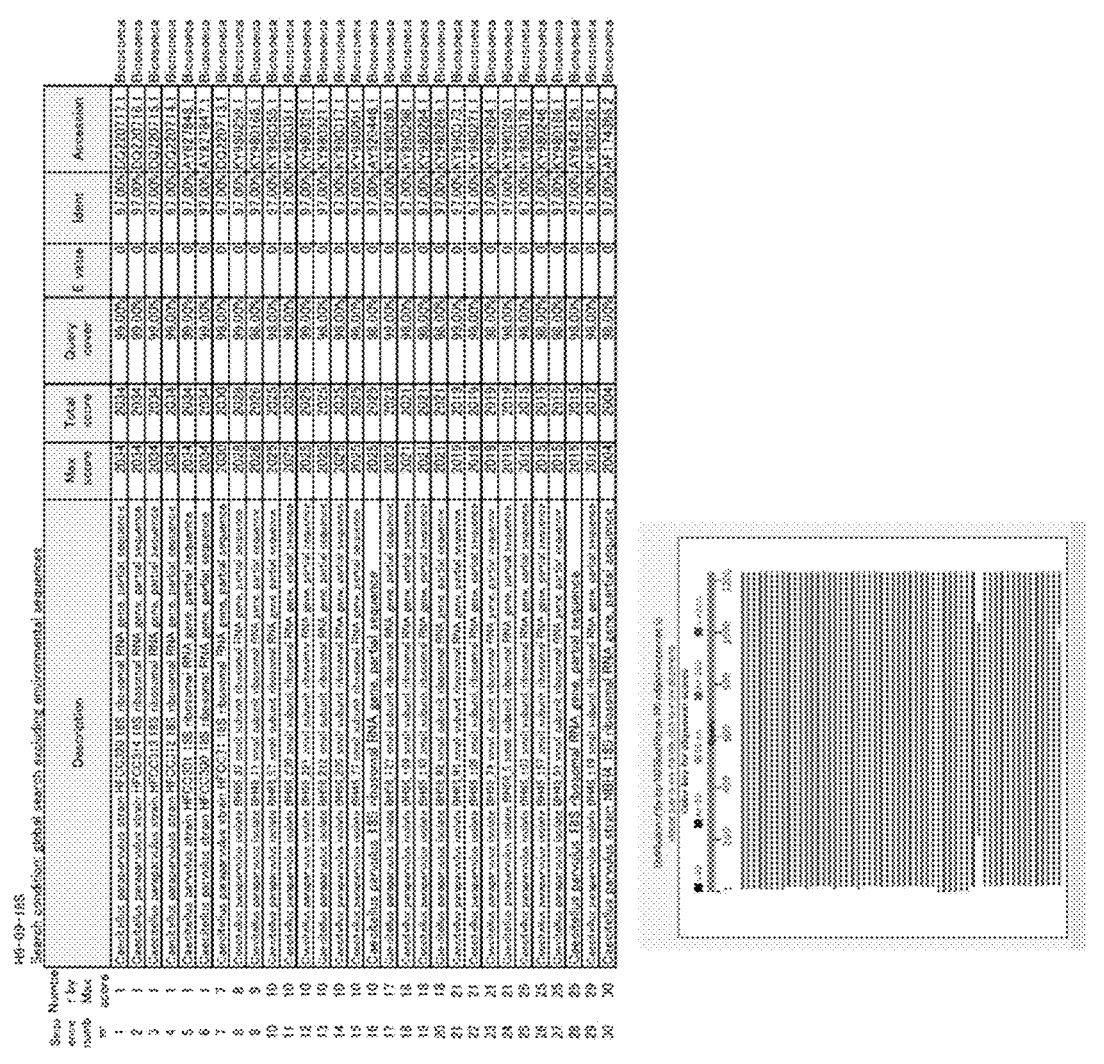
Figure 23:
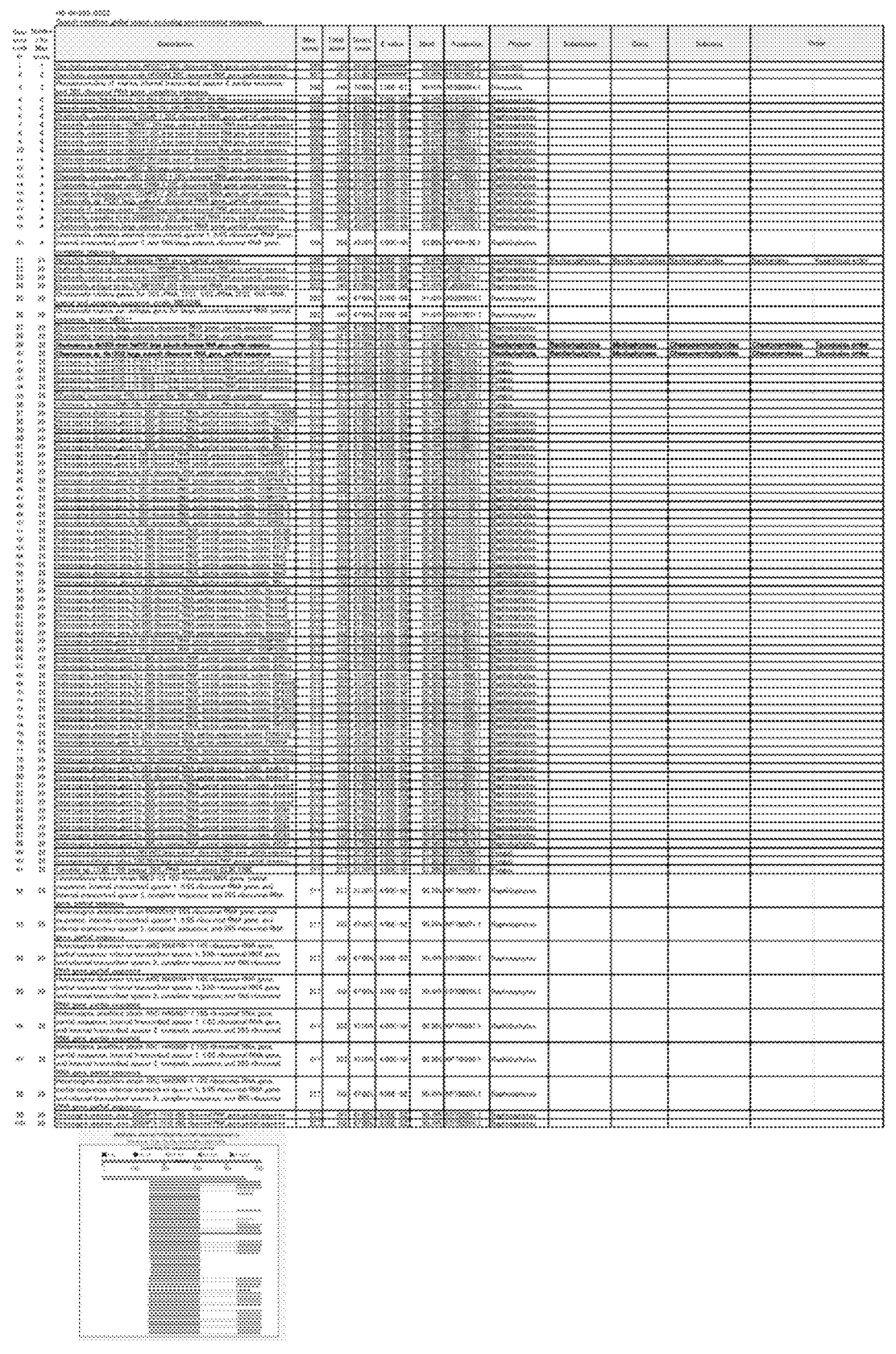
Figure 24:
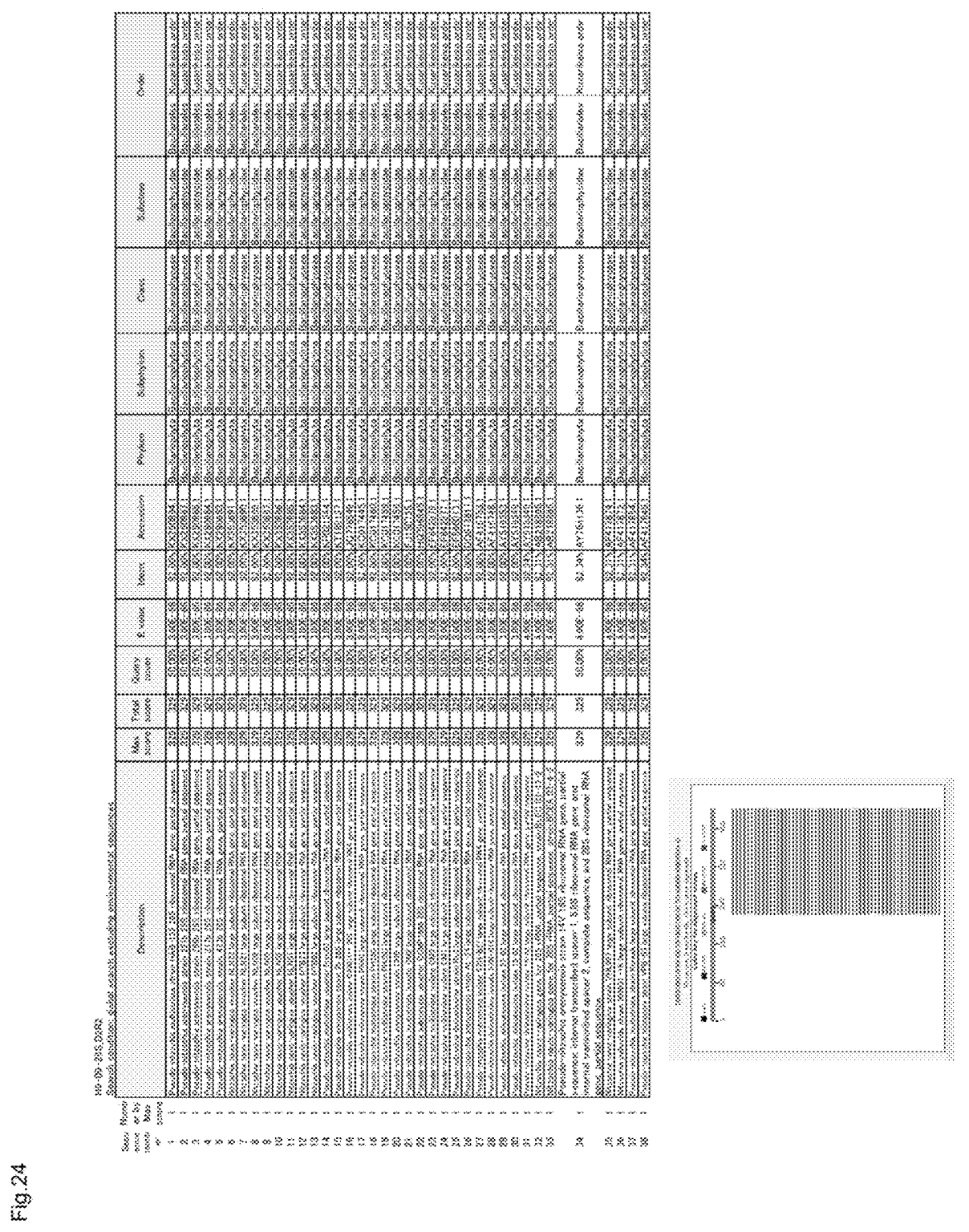

| Site | Sequence name | Base sequence length used for analysis | Sequence assembly | Blast analysis result |
|------|---------------|----------------------------------------|-------------------|----------------------|
| 18S | H9-09-18S | 1228 bp | Performed | FIG. 22 |
| 28S | H9-09-28S-D2C2 | 511 bp | Not performed | FIG. 23 |
| 28S | H9-09-28S-D2R2 | 441 bp | Not performed | FIG. 24 |

(megaBLAST Search Result)
18S
The homology with the sequence of Caecitellus paraparvulus HFCC320 strain (bicosoeca) was 97%.
For each of the second and subsequent orders, the homology with the diatom in the same genus was 97%
While the homology is slightly low at 97%, the possibility that the sequence of bicosoeca was amplified cannot be denied.
However, in the microscopic examination performed in advance, it is confirmed that the specimen has a shape like a diatom.
Sequence of 28S D2C2
The homology with the sequence of Caecitellus paraparvulus HFCC71 strain (bicosoeca) was 88%.
The homology is less than 90%. Since the sequence is short, and both the score and the cover rate are low, the degree of reliability on the classification result is considerably low compared with the result of 18S.
Therefore, it is excluded from this examination on the classification.
However, it is consistent with the result of 18S (being bicosoeca).
Sequence of 28S D2R2
The homology with the sequence of Pseudo-nitzschia multistriata HAB-132 strain (subclass Bacillariophycidae) was 92%,
The homology is low at 92%. Since the sequence is short, and both the score and the cover rate are low, the degree of reliability on the classification result is low compared with the result of 18S.
However, it is consistent with the morphology observation performed in advance (being a diatom).
(Classification Result)
Undetermined

DESCRIPTION OF REFERENCE SIGNS

1 Plankton
4 GF/C filter
5 Container

The invention claimed is:
1. A method for producing 3,5-dihydroxy-4-methoxybenzyl alcohol from plankton, the method comprising:
filtering collected seawater containing the plankton using a filter;
taking out a cell content from the plankton remained on the filter; and
subsequently heating the cell content thus taken out to produce 3,5-dihydroxy-4-methoxybenzyl alcohol from the heated material,
wherein the plankton is a diatom belonging to phylum Bacillariophyta, subphylum Bacillariophytina, class Bacillariophyceae, subclass Bacillariophycidae, order Surirellales, family Entomoneidaceae, genus *Entomoneis*.
2. The method according to claim 1,
wherein the cell content is heated at a temperature of 60° C. for one hour to four hours.
3. The method according to claim 1,
wherein the cell content is heated at a temperature of 80° C. for 30 minutes to one hour or three hours to five hours.
4. A method for producing 3,5-dihydroxy-4-methoxybenzyl alcohol from plankton, the method comprising:
filtering collected seawater containing the plankton using a filter;
crushing the plankton remained on the filter with an addition of an extracting solution; and
extracting a cell content from the plankton and subsequently performing heating or pressurization to produce 3,5-dihydroxy-4-methoxybenzyl alcohol from the heated material,
wherein the plankton is a diatom belonging to phylum Bacillariophyta, subphylum Bacillariophytina, class Bacillariophyceae, subclass Bacillariophycidae, order Surirellales, family Entomoneidaceae, genus *Entomoneis*.
5. The method according to claim 4,
wherein the step of subsequently performing heating or pressurization is a step of heating, and
wherein the cell content is heated at a temperature of 60° C. for one hour to four hours.
6. The method according to claim 4,
wherein the step of subsequently performing heating or pressurization is a step of heating, and
wherein the cell content is heated at a temperature of 80° C. for 30 minutes to one hour or three hours to five hours.
7. The method according to claim 4,
wherein the step of subsequently performing heating or pressurization is a step of pressurization, and
wherein the cell content is pressurized at 2 atmospheres for 30 minutes.
8. The method according to claim 4,
wherein the step of subsequently performing heating or pressurization is a step of pressurization, and
wherein the cell content is pressurized at 2.5 atmospheres for 30 minutes or more.
9. The method according to claim 4,
wherein the step of subsequently performing heating or pressurization is a step of pressurization, and
wherein the cell content is pressurized at 3 atmospheres for 30 minutes or more.
10. A method for producing 3,5-dihydroxy-4-methoxybenzyl alcohol from plankton, the method comprising:

filtering collected seawater containing the plankton using a filter;

taking out a cell content from the plankton remained on the filter; and subsequently pressurizing the cell content thus taken out to produce 3,5-dihydroxy-4-methoxybenzyl alcohol from the pressurized material, wherein the plankton is a diatom belonging to phylum Bacillariophyta, subphylum Bacillariophytina, class Bacillariophyceae, subclass Bacillariophycidae, order Surirellales, family Entomoneidaceae, genus *Entomoneis*.

11. The method according to claim 10, wherein the cell content is pressurized at 2 atmospheres for 30 minutes.

12. The method according to claim 10, wherein the cell content is pressurized at 2.5 atmospheres for 30 minutes or more.

13. The method according to claim 10, wherein the cell content is pressurized at 3 atmospheres for 30 minutes or more.

* * * * *